(12) United States Patent
Boda et al.

(10) Patent No.: US 12,014,811 B2
(45) Date of Patent: Jun. 18, 2024

(54) SYSTEMS AND METHODS FOR CACHING BIOLOGICAL IMAGE DATA

(71) Applicant: Ventana Medical Systems, Inc., Tucson, AZ (US)

(72) Inventors: Prakash Boda, Santa Clara, CA (US); Abhisheak Sharma, Santa Clara, CA (US); Steve Yungming Yu, Santa Clara, CA (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 572 days.

(21) Appl. No.: 17/274,060

(22) PCT Filed: Sep. 3, 2019

(86) PCT No.: PCT/US2019/049289
§ 371 (c)(1),
(2) Date: Mar. 5, 2021

(87) PCT Pub. No.: WO2020/051113
PCT Pub. Date: Mar. 12, 2020

(65) Prior Publication Data
US 2021/0358596 A1    Nov. 18, 2021

Related U.S. Application Data

(60) Provisional application No. 62/728,573, filed on Sep. 7, 2018.

(51) Int. Cl.
| | | |
|---|---|---|
| *G16H 30/20* | (2018.01) | |
| *G06F 3/06* | (2006.01) | |
| *G06F 21/62* | (2013.01) | |

(52) U.S. Cl.
CPC ........... *G16H 30/20* (2018.01); *G06F 3/0608* (2013.01); *G06F 3/0616* (2013.01);
(Continued)

(58) Field of Classification Search
None
See application file for complete search history.

(56) References Cited

U.S. PATENT DOCUMENTS

| | | |
|---|---|---|
| 7,087,379 B2 | 8/2006 | Light |
| 8,970,618 B2 | 3/2015 | Ruddle et al. |
| 9,439,565 B1 | 9/2016 | Chai et al. |

(Continued)

FOREIGN PATENT DOCUMENTS

| | | |
|---|---|---|
| CN | 107004059 A | 8/2017 |
| JP | 2013105204 | 5/2013 |
| WO | 2018/115055 | 6/2018 |

OTHER PUBLICATIONS

Application No. JP2021-512480, Office Action, dated Mar. 28, 2023, 5 pages.

(Continued)

*Primary Examiner* — Jiangeng Sun
(74) *Attorney, Agent, or Firm* — Kilpatrick Townsend & Stockton LLP

(57) ABSTRACT

The present disclosure is directed to digital pathology systems and server systems, each of which may comprise caches pre-populated with biological image data, including biological image data which was been pre-processed into a destination file format. Caches can be populated with biological image data on the digital pathology system and/or server system for retrieval of biological image data, facilitating real-time or near real-time visualization of biological image data in a browser or on the digital pathology system. Biological image data on a server can be automatically pre-processed as scanned image data is received.

25 Claims, 16 Drawing Sheets

(52) U.S. Cl.
CPC ............ *G06F 3/0631* (2013.01); *G06F 3/068* (2013.01); *G06F 21/6209* (2013.01)

(56) References Cited

U.S. PATENT DOCUMENTS

| | | | |
|---|---|---|---|
| 9,569,463 B1 | 2/2017 | Nourse et al. | |
| 2007/0226314 A1* | 9/2007 | Eick | G06F 16/986 709/217 |
| 2011/0015494 A1* | 1/2011 | Spaulding | G16H 40/63 356/402 |
| 2012/0320094 A1* | 12/2012 | Ruddle | G16H 30/20 345/660 |
| 2014/0250156 A1* | 9/2014 | Chatry | G06F 16/137 707/827 |
| 2016/0267649 A1 | 9/2016 | Hu et al. | |

OTHER PUBLICATIONS

Application No. JP2021-512480, Office Action, dated Sep. 27, 2022, 9 pages (pp. 1-5 English translation, pp. 6-9 original document).

International Search Report received in International Patent Application No. PCT/US2019/049289, dated Dec. 5, 2019.

Tuominen, et al., "Linking Whole-Slide Microscope Images with DICOM by Using JPEG2000 Interactive Protocol", *Journal of Digital Imaging: The Journal of the Society for Computer Applications in Radiology*, Springer-Verlag, NE, vol. 23, No. 4, May 4, 2009, pp. 454-462.

Japanese Application No. 2021-512480, Office Action dated Mar. 17, 2022, 16 pages (7 pages of Original Document and 9 pages of English Translation).

International Application No. PCT/US2019/049289, Invitation to Pay Additional Fees and, Where Applicable, Protest Fee dated Dec. 19, 2019, 14 pages.

Zamay et al., Current and Prospective Biomarkers of Lung Cancer, Cancers (Basel), vol. 9, No. 11, Nov. 2018.

CN Application No. 201980058393.2, "Office Action", dated Oct. 27, 2023, 19 pages.

JP Application No. 2021-512480, "Notice of Allowance", dated Jul. 12, 2023, 6 pages.

EP Application No. 19769341.9, "Office Action", Mar. 22, 2024, 6 pages.

\* cited by examiner

SYSTEMS AND METHODS FOR CACHING BIOLOGICAL IMAGE DATA

CROSS-REFERENCE TO RELATED APPLICATIONS

This application is the U.S. National Phase of International Patent Application No. PCT/US2019/049289, filed Sep. 3, 2019, which claims the benefit of U.S. Patent Provisional Application No. 62/728,573, filed Sep. 7, 2018, which are i-s incorporated herein by reference in their entireties for all purposes.

BACKGROUND

Digital pathology refers to the management and interpretation of pathology information in a digital environment. Scanning devices are used to image slides of biological samples, which may be stained, such that digital slides, e.g., whole slide images, are generated. Digital pathology software enables digital slides to be stored in a computer memory device, viewed on a computer monitor, and analyzed for pathology information.

SUMMARY

The present disclosure is directed, among other things, to a client-server system including a client user interface (GUI) having improved response time. In general, an interface for the visualization and analysis of image data is run on (i) a client system (e.g. a viewer application run locally on the client system), or (ii) on a remote server where the client system accesses an instance of the viewer application on the remote server via a browser, such as a web browser. Image data, e.g. scanned images of biological samples stained with hematoxylin and eosin or stained for the presence of one or more biomarkers, may be delivered to the viewer application or browser from a remote server, e.g. from a storage system communicatively coupled to the remote server. In some embodiments, the image data is in the form of image tiles (defined herein) which may be delivered to the viewer application or browser. Because of the quantity of image tiles that are generally transferred from the remote server (not to mention the size of the files transmitted), image data may not be visualized in real-time within the viewer application or browser after a user input is received by the viewer application. This could hinder the user's ability to perform an analysis of the image data in real-time.

To better facilitate image visualization, the present disclosure provides, in some embodiments, for the automated pre-processing of biological image data (e.g. histopathology image data or cytopathology image data) on a server and the delivery of the pre-processed image data to a client system, e.g. a digital pathology analysis system. In some embodiments, the pre-processing of the image data comprises converting scanned image data from an input format (e.g. DICOM, BIF, or another uncompressed image file format) to a destination format (e.g. a compressed image file format, such as a JPEG). It is believed that the image data included within the input format is large, e.g. over 2000 megabytes per image file, and converting the input file format to a destination file format (where the data may be compressed) enables quicker delivery of image data to a client system. In some embodiments, the pre-processing of image data comprises splitting a scanned image data file into multiple files (e.g. a plurality of image tile files which may either be in the input file format or in a destination file format), again facilitating a quicker delivery of image data from a server to a client system. It is believed that severs have finite processing power, which may be taxed if multiple requests for image data (such as from one or more client systems) are received in real-time. By pre-processing image data on the sever prior to a request for image data from a client system, server resources, such as processing resources, will be less taxed, enabling for improved delivery of image data to client systems. For example, instead of generating image tiles in real-time in response to a user request or a pre-fetching operation, the biological image data may be pre-processed and image tiles may be immediately available for transmission.

The present disclosure also provides, in some embodiments, for the automated delivery of biological image data, including pre-processed image data in a destination file format, from a server to a client cache communicatively coupled to a client system, such as via a cache agent. In this way, image data requested from a client system may be retrieved from a local client cache pre-populated with image data, such as pre-processed image data, rather than have to be transmitted over a network, which could be slow given the file sizes involved. Overall, the systems and methods described herein provide for a more robust and accurate review of image data, ultimately providing for improved patient care. Moreover, the systems and methods described herein provide a better user experience, enabling the user (e.g. a pathologist) to perform their duties more quickly and accurately.

In one aspect of the present disclosure is a method of pre-processing biological image data on a server to facilitate the transmission of the biological image data to a digital pathology analysis system, comprising: receiving the biological image data having a first image file format, the biological image data derived from scans of microscope slides having one or more biological samples disposed thereon, the biological samples stained with hematoxylin and eosin or stained for the presence of one or more biomarkers; pre-processing the received biological image data to generate one or more pre-processed image files, each of the generated one or more pre-processed image files derived from the received biological image data in the first file format, and wherein each of the generated one or more pre-processed image files are provided in a second file format; and storing the generated one or more pre-processed image files provided in the second file format in one or more memories communicatively coupled to the server.

In some embodiments, the first image file format and the second image file format are the same. In some embodiments, the pre-processing step generates a plurality of pre-processed image files. In some embodiments, the plurality of pre-processed image files are a plurality of image tile files, and wherein the stored plurality of image tile files each comprise a file name comprising coordinates corresponding to a position of an individual tile file within the received biological image data having the first image file format. In some embodiments, pre-processing step generates multiple sets of pre-processed image files, wherein each set of pre-processed image files of the multiple sets of pre-processed image files comprises a plurality of image tile files corresponding to a single magnification level. In some embodiments, the first and second file formats are compressed image file formats. In some embodiments, the compressed image file formats are selected from the group consisting of JPEG File Interchange Format, portable network graphics file format, and derivates thereof.

In some embodiments, the first image file format and the second image file format are different. In some embodiments, the first image file format is one of a RAW image file format or an uncompressed image file format; and wherein the second image file format is a compressed image file format. In some embodiments, the pre-processing step comprises converting the received biological image data in the RAW or uncompressed image file format and generating the one or more pre-processed image files in the compressed image file format. In some embodiments, the pre-processing step generates a single pre-processed image file in the compressed image file format. In some embodiments, the pre-processing step generates a plurality of pre-processed image files in the compressed image file format. In some embodiments, the pre-processing step generates multiple sets of pre-processed image files, wherein each set of pre-processed image files of the multiple sets of pre-processed image files comprises a plurality of image tile files in the compressed image file format corresponding to a single magnification level. In some embodiments, the plurality of pre-processed image files are a plurality of image tile files, and wherein the stored plurality of image tile files each comprise a file name comprising coordinates corresponding to a position of an individual tile file within the received biological image data having the first image file format. In some embodiments, a file size of the received biological image data having the first file format is greater than an aggregate file size of all of the generated plurality of the pre-processed image files in the compressed image file format. In some embodiments, the compressed image file format is a destination file format. In some embodiments, the destination file format is a browser compatible file format.

In some embodiments, the method further comprises receiving a request from the digital pathology analysis system for the stored one or more pre-processed image files. In some embodiments, the method further comprises automatically transferring the stored one or more pre-processed image files to a cache agent running on a digital pathology analysis system. In some embodiments, the one or more memories comprise both volatile and non-volatile memories. In some embodiments, the one or more memories are non-volatile memories. In some embodiments, the stored one or more pre-processed image files are maintained in the one or more non-volatile memories for a pre-determined amount of time. In some embodiments, the predetermined amount of time ranges from between about 5 days to about 15 days.

In another aspect of the present disclosure is a method of managing biological image data in a client cache within a digital pathology analysis system, comprising: performing a user authentication with a remote server, wherein the authentication comprises confirming that a cache agent is running on the digital pathology analysis system; receiving a plurality of new biological image tiles from the remote server, the new biological image tiles derived from scans of microscope slides having one or more biological samples disposed thereon, the biological samples stained with hematoxylin and eosin or stained for the presence of one or more biomarkers; removing at least a first portion of pre-existing biological image tiles from a client cache communicatively coupled to the digital pathology system based on predetermined criteria; and storing the received new biological image tiles in the client cache.

In some embodiments, the pre-determined criteria comprises storage allocation limits, cache image expirations, slide viewing period expirations, and case reassignment. In some embodiments, an aggregate size of the first portion of pre-existing biological image tiles removed is about the same as a total size of the new biological image tiles received. In some embodiments, an aggregate size of the first portion of pre-existing biological image tiles removed is greater than a size of the new biological image tiles received. In some embodiments, the received plurality of new biological image tiles are pre-processed biological image tiles having a compressed file format. In some embodiments, the compressed file format is JPEG.

In some embodiments, the method further comprises maintaining the client cache by removing a first portion of the stored new biological image tiles based on predetermined criteria. In some embodiments, the pre-determined criteria comprises storage allocation limits, cache image expirations, slide viewing period expirations, and case reassignment. In some embodiments, the method further comprises removing a second portion of the stored new biological image tiles which were reviewed by a pathologist.

In another aspect of the present disclosure is a method of managing biological image data in a client cache within a digital pathology analysis system, comprising: maintaining a client cache communicatively coupled to the digital pathology analysis system, the client cache comprising biological image data for one or more patient cases, wherein the client cache is maintained by removing a first portion of the pre-existing biological image data based on predetermined criteria; performing an authentication with a remote server; receiving a first request from the remote server to add new biological image data to the client cache; and storing the received new biological image data in the client cache, and where the pre-existing biological image data and the stored new biological image data are derived from scans of microscope slides having one or more biological samples disposed thereon, the biological samples stained with hematoxylin and eosin or stained for the presence of one or more biomarkers.

In some embodiments, the pre-determined criteria comprises storage allocation limits, cache image expirations, slide viewing period expirations, and case reassignment. In some embodiments, the client cache is further maintained by removing a second portion of the pre-existing biological image data for the one or more patient cases which were reviewed by a pathologist assigned to the one or more patient cases.

In some embodiments, the client cache is pre-allocated on a storage subsystem communicatively coupled to the digital pathology analysis system. In some embodiments, the authentication comprises confirming that the cache agent is running on the digital pathology analysis system.

In some embodiments, the method further comprises receiving a second request from a viewer application or a browser running on the digital pathology analysis system to retrieve at least a portion of the stored new biological image data from the client cache. In some embodiments, the retrieved stored new biological image data is transferred to the viewer application or the browser and displayed on a display screen of the digital pathology analysis system. In some embodiments, the stored new biological image data comprises a plurality of pre-processed image tiles in a compressed image file format. In some embodiments, plurality of image tiles comprise a first series of image tiles corresponding to biological image data scanned at a first magnification level and a second series of image tiles corresponding to biological image data scanned at a second magnification level.

In another aspect of the present disclosure is a method of maintaining cached biological image data in a client cache communicatively coupled to a digital pathology analysis system, comprising: accessing the biological image data, wherein the biological image data is derived from scans of microscope slides having one or more biological samples disposed thereon, the biological samples stained with hematoxylin and eosin or stained for the presence of one or more biomarkers; receiving a confirmation that a cache agent is running on the digital pathology analysis system; delivering at least a portion of the accessed biological image data to at least partially fill a portion of available storage space within the client cache; and storing one or more URLs associated with the at least the portion of the accessed biological image data delivered to the digital pathology analysis system.

In some embodiments, the at least the portion of the accessed biological image data is delivered to completely fill the available storage space on the client server. In some embodiments, the at least the portion of accessed biological image data delivered to the client cache comprises a plurality of pre-processed image tiles in a compressed image file format. In some embodiments, the plurality of pre-processed image tiles comprise a first series of pre-processed image tiles at a first magnification level and a second series of pre-processed images tiles at a second magnification level. In some embodiments, the method further comprises receiving an indication that sufficient available storage space exists within the client cache prior to delivering the at least the portion of the accessed biological image data. In some embodiments, the method further comprises receiving an indication of a quantity of available storage space within the client cache. In some embodiments, the delivering of the at least the portion of the accessed biological image data comprises (i) determining the size of the accessed biological image data; and (ii) selecting the at least the portion of the accessed biological image data based on the available storage space within the client cache. In some embodiments, the selecting of the at the portion of the accessed biological image data is based on predetermined selection criteria. In some embodiments, the predetermined selection criteria are scanning dates of individual images within the accessed biological image data. In some embodiments, the accessed biological image data is assigned to a first pathologist on the digital pathology analysis system. In some embodiments, the step of authentication further comprises confirming identification credentials of the first pathologist. In some embodiments, the server maintains a connection to the cache agent, and wherein the step of receiving a confirmation that a cache agent is running on the client system comprises confirming that the connection is established.

In another aspect of the present disclosure is a method of displaying biological image data in an interface application on a digital pathology analysis system, comprising: receiving a first user input pertaining to a first patient case; contacting a remote server for one or more stored biological image tiles corresponding to the received first user input, wherein the stored biological image data is derived from scans of microscope slides having one or more biological samples disposed thereon, the biological samples stained with hematoxylin and eosin or stained for the presence of one or more biomarkers; receiving location information for the one or more stored biological image tiles corresponding to the first user input; retrieving the one or more stored biological image tiles pertaining to the first user input based on the received location information; and visualizing the retrieved one or more biological image tiles pertaining to the first user input.

In some embodiments, the method further comprises the step of determining whether the stored one or more biological image tiles are present within a client cache communicatively coupled to the digital pathology analysis system. In some embodiments, the stored one or more biological image tiles are retrieved from the client cache if the biological image data has been maintained within the client cache. In some embodiments, the stored one or more biological image tiles are retrieved from the remote server if the image was removed from the client cache. In some embodiments, the stored one or more biological image tiles retrieved from the remote server are downloaded to the client cache. In some embodiments, the visualized one or more biological image tiles are retrieved from the client cache. In some embodiments, if the stored one or more biological image tiles have not been maintained in the client cache, the interface is redirected to a storage location on the remote server. In some embodiments, the stored one or more biological image tiles pertaining to the first user input are retrieved from the remote server, and further comprising receiving a second user input pertaining to the first patient case, and wherein one or more stored image tiles pertaining to the second user input are retrieved from the client cache. In some embodiments, the stored one or more biological image tiles are pre-processed image tiles in an uncompressed format. In some embodiments, the method further comprises managing the client cache by removing pre-populated biological image data meeting predetermined criteria. In some embodiments, the location information comprises one or more URLs.

BRIEF DESCRIPTION OF THE FIGURES

For a general understanding of the features of the disclosure, reference is made to the drawings. In the drawings, like reference numerals have been used throughout to identify identical elements.

The patent or application file contains at least one drawing executed in color. Copies of this patent or patent application publication with color drawings will be provided to the Office upon request and the payment of the necessary fee.

DETAILED DESCRIPTION

Figure 1A:
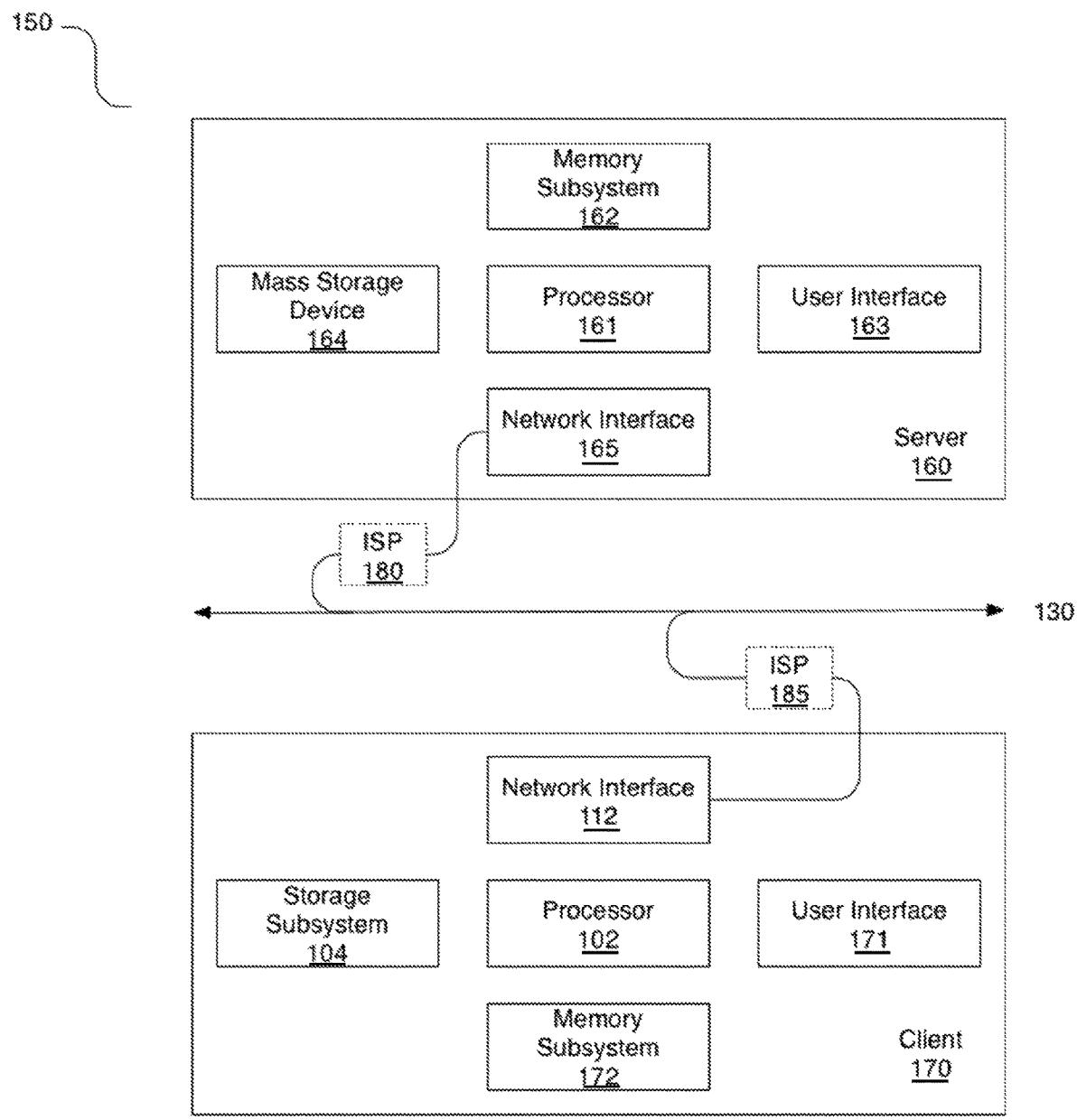
FIG. 1A illustrates a client-server system including a server 160 communicatively coupled to a client system 170, such as through a network in accordance with some embodiments.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of," when used in the claims, shall have its ordinary meaning as used in the field of patent law.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "cytopathology" refers to the studies of diseases at the cellular level, such as samples of free cells or tissue fragments.

As used herein, the term "DICOM" refers to a standard for handling, storing, printing, and transmitting information in medical imaging. It includes a file format definition and a network communication protocol. The network communication protocol is an application protocol that uses TCP/IP to communicate between systems. One of the goals of the standard is to make uniform the transferring of medical images and information between viewing and scanning sources to allow users of different imaging software and/or hardware to share information. DICOM files can be exchanged between two entities that are capable of receiving image and patient data in DICOM format. DICOM enables the integration of scanners, servers, workstations, printers, and network hardware from multiple manufacturers into a Picture Archiving and Communication System (PACS) for storing and downloading of digital images. The different devices come with DICOM conformance statements that clearly state the DICOM classes they support. DICOM has been widely adopted by hospitals and is gaining popularity in smaller dentists' and doctors' offices. DICOM files commonly contain images; therefore, they are often referred to as DICOM images. But it will be understood that a DICOM file does not necessarily need to include an image. Rather, such a file can include measurements or report data. Thus, DICOM files may contain media data, such as, video and audio data, or no media data at all. In that case, DICOM files may contain only metadata identifying the originating modality, the operator, or the patient being examined. Modality here refers to any image generating equipment in medical imaging and also includes the use of scanners to generate images of histopathology slides or cytopathology slides, such as those stained with hematoxylin and eosin or for the presence of one or more biomarkers.

As used herein, the term "histopathology" refers to the microscopic examination of tissue (e.g. a biopsy specimen, a surgical specimen) to study manifestations of disease.

As used herein, the term "image data" encompasses raw image data acquired from the biological tissue sample, such as by means of an optical sensor or sensor array, or pre-processed image data. In particular, the image data may comprise a pixel matrix. In some embodiments, image data is stored in blocks of image tiles (e.g. portions of a whole slide image having a size of about 500 pixels by about 500 pixels). In some embodiments, image data is derived from scans of biological samples disposed on a substrate (e.g. a microscope slide), and the scanned of the biological samples may include multiple images of the same slide at different levels of magnification (e.g. 20×, 40×, etc.). In some embodiments, image data is captured at a first, low level magnification (e.g. suitable for a thumbnail image); at a second, intermediate magnification level; and at a third, high magnification level. In some embodiments, the image data may be acquired for a plurality of magnification levels and one or more image data files may be generated for each of the plurality of magnification levels. In some embodiments, the number of image tiles increases with the magnification level or zoom level, i.e. image tiles may be available for each of a predetermined number of available magnification levels and those higher magnification levels will have a greater number of images tiles than those at lower magnification levels. In some embodiments, the number of tiles at each zoom level increases, e.g., linearly, quadratically, exponentially, or otherwise. For example, lowest magnification image data (corresponding to the above-mentioned first magnification level) may comprise a hundred toles, whereas an intermediate magnification image data may comprise four hundred tiles.

As used herein, the term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1-inch microscope slide or a standard 75 mm by 25 mm microscope slide. Examples of biological specimens that can be placed on a slide include, without limitation, a cytological smear, a thin tissue section (such as from a biopsy), and an array of biological specimens, for example a tissue array, a cellular array, a DNA array, an RNA array, a protein array, or any combination thereof. Thus, in one embodiment, tissue sections, DNA samples, RNA samples, and/or proteins are placed on a slide at particular locations. In some embodiments, the term slide may refer to SELDI and MALDI chips, and silicon wafers.

As used herein, the terms "stain," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the term "user interface" refers to the interface that allows the user, for example end users such as histologists and/or pathologists, to input commands and data and receive results, such as a graphical user interface (GUI). The terms "user interface" and "graphical user interface" are used interchangeably herein.

Overview

Pathology images are typically very large, e.g. more than 1000 megabytes, more than 2000 megabytes each. For example, a high resolution slide image can have a resolution of 100,000 by 80,000 pixels. Such large images are often too large to be efficiently transmitted over a network, especially over a network and through an internet service provider. To mitigate the effect of network latency in visualizing image data in a viewer application, image data, such as in the form of image tiles (including as pre-processed image tiles as described herein), is pre-fetched and transferred from a remote server to the viewer application 120 based on user inputs. It is believed that the use of tiles to break down the larger blocks of image data greatly improves the efficiency of image data transfer over network, since only those tiles or portions of tiles corresponding to a specific selected magnification need to be transferred, versus transmitting the whole slide image.

Pre-fetching refers to requesting image data from a remote storage system or database, such as that of remote server, prior to any specific user request for image data, so that image data may be collected and buffered on a device until a specific user request for image data. In this way, pre-fetching seeks to collect image data in the background, before that image data is actually called upon to construct a visualization on display, thereby reducing (and even eliminating) the need for client system to request image data only after a user request. The pre-fetched image data is automatically identified, requested, and stored within a pre-allocated memory of a viewer application or browser for subsequent use in constructing a visual display. In some embodiments, the pre-fetched data comprises image tiles, such as a plurality of image tiles at a certain magnification level.

In some embodiments, pre-fetching is based on a prediction of user inputs, e.g. using a user's past actions, selections, and inputs to anticipate further actions, selections, and inputs, i.e. when a user input is received via a user interface, image data for the next few levels of possible user inputs is also pre-fetched. The viewer application or browser may routinely pre-fetch image data comprising a plurality of image tiles based on user inputs and/or anticipated user inputs. When a user interacts with the visualizations displayed within viewer application or browser, the user may wish to pan around to visualize other image data near any first visualized image data. Therefore, the viewer application or browser uses a system to pre-fetch and store a sufficient amount of image data (e.g. image tiles) to provide the requested visualization while buffering additional image data within the memory of the viewer application or browser allow efficient user interaction with that visualization. By way of example, if viewer application or browser determines that a user is panning an image in a particular direction, image tile data may be pre-fetched along the path general path that the user is panning. Additional methods of visualizing and pre-fetching tiles of data are described in U.S. Pat. Nos. 9,569,463 and 8,970,618, the disclosures of which are hereby incorporated by reference herein in their entireties.

As noted above, the pre-fetching of data is limited to the available memory resources allocated to the interface application, e.g. the viewer application 120 or browser 195, running on the client system 170. Such memory allocations can be insufficient to provide real time visualization and analysis of image data based on user inputs. In some embodiments, a client cache and/or server cache (where each may include pre-processed image data) can be used to expand upon the memory available to a viewer application 120 or browser 195. As described herein, a greater number of image tiles may be stored in a client cache than may be comparatively stored in a memory allocated to a viewer application 120 or browser 195. In fact, entire images within in a patient case record, an entire patient case record, or even a plurality of patient case records (each having a plurality of images and associated image tiles at one or more magnification levels) may be stored in a client cache (such as one managed by a cache agent 140) for retrieval by viewer application 120 or browser 195. Such a cache of maintained image data enables a quicker retrieval or pre-fetching of image data as compared with retrieving pre-fetched image data from a remote server over network 130.

To facilitate the provisioning of image data and to speed up the visualization of such image data, in some embodiments, a client cache (e.g. a cache coupled to a digital pathology analysis system) is provided that stores image data in a storage subsystem communicatively coupled to the client system. In some embodiments, the client cache is managed by a cache agent, e.g. one that determines those sets of received and stored image data to retain or discard from the cache, such as based on pre-established and/or user configurable criteria. In some embodiments, this image data is automatically pushed from a server to the client system (such as through a "cache agent" application running on the client system). In this way, a client cache coupled to the client system is pre-populated with image data, such as newly scanned image data as it is received by the server or after it is first pre-processed by the server. In some embodiments, the client cache enables improved visualization and analysis of requested and/or presented image data since the image data may be pre-fetched or retrieved quickly from the client cache coupled to the client system and not from remote server (i.e. image data is retrieved locally from a pre-populated client cache, as opposed to over a network). As a result, latency is improved (see the Examples herein). It is also believed that this may also free up sever resources since the server will not be needed to fetch and transmit data or as much data. Moreover, it is believed that through the use of such a client cache, a user will not be limited by available network or internet service provider bandwidth, allowing for quicker and more efficient visualization and analysis of image data.

Another modality for improving the transmission of image data for visualization and analysis is through the implementation of a server-side pre-processing routine, where received scanned image data, such as in an input file format (e.g. DICOM, BIF, or another uncompressed image file format), is converted to a destination file format prior to storage in a server cache or transmission to a client system. In some embodiments, the destination file format is one that is readable by a standard web browser running on a client system, i.e. in a format that is recognizable by a web browser without any further conversion or the use of any further image reading applications. In some embodiments, the input image data may also be broken down into smaller files, which may be stored in a server cache (and which pre-processed image data may be pre-fetched on an as-needed basis) or transmitted to a client system either in real-time upon a user request or pre-transmitted to a client cache. The use of such pre-processing of image data on a server enables more efficient use of server resources (e.g. pre-processing of image data as it is received versus in real-time upon a request) and also enables the quicker transmission of such data to a client system (e.g. using a compressed image file format or multiple image files, each in a compressed image file format).

The systems and methods provided herein can be applied to the visualization and analysis of any type of image of a biological specimen, including histopathology specimens and/or cytopathology specimens. In some embodiments, a tissue sample is stained with hematoxylin and eosin or stained for the presence of one or more biomarkers. For example, the biological sample may be stained through application of one or more stains, and the resulting image or image data comprises signals corresponding to each of the one or more stains. In some embodiments, the input images are simplex images having only a single stain (e.g., stained with 3,3'-diaminobenzidine (DAB)). In some embodiments, the biological sample may be stained in a multiplex assay for two or more stains (thus providing multiplex images). In some embodiments, the biological samples are stained for at least two biomarkers. In some embodiments, the biological samples are stained for the presence of at least two biomarkers and also stained with a primary stain (e.g. hematoxylin). In some embodiments, the biological samples are stained for the presence of at least one protein biomarker and at least two nucleic acid biomarkers (e.g. DNA, RNA, microRNAs, etc.).

In some embodiments, the biological samples are stained in an immunohistochemistry assay for the presence of one or more protein biomarkers. For example, the biological sample may be stained for the presence of a human epidermal growth factor receptor 2 protein (HER2 protein) (e.g. HerceptTest™ (DAKO, Glostrup Denmark) and HER2/neu (4B5) rabbit monoclonal primary antibody (Ventana, Tucson, Arizona).

In some embodiments, the biological sample is stained for the presence of estrogen receptor (ER), progesterone receptor (PR), or Ki-67. In some embodiments, the biological sample is stained for the presence of EGFR or HER3. Examples of other protein biomarkers are described by Zamay et. Al., "Current and Prospective Biomarkers of Long Cancer," Cancers (Basel), 2018 November; 9(11), the disclosure of which is hereby incorporated by reference herein in its entirety. Examples of protein biomarkers described by Zamay include CEACAM, CYFRA21-1, PKLK, VEGF, BRAF, and SCC.

In some embodiments, the biological samples are stained in an in situ hybridization (ISH) assay for the presence of one or more nucleic acids, including mRNA. U.S. Pat. No. 7,087,379 (the disclosure of which is hereby incorporated by reference herein in its entirety) describes methods of staining samples with ISH probes such that individual spots (or dots), representing single gene copies, may be observed and detected. In some embodiments, several target genes are simultaneously analyzed by exposing a cell or tissue sample to a plurality of nucleic acid probes that have been labeled with a plurality of different nucleic acid tags.

In some embodiments, systems of the present disclosure are adapted to facilitate the visualization, analysis, and reporting of biological image data obtained from a subject (e.g. a biopsy sample obtained from a human patient). Exemplary client-server systems 150 are depicted in FIGS. 1A-1D and include a server 160 and a client system 170 (e.g. a digital pathology analysis system) that are coupled together via a network 130, which may be, for example, the Internet or an intranet. The server 160 includes a processor 161 coupled to a memory subsystem 162, a user interface 163, a mass storage device 164 and a network interface 165. In some embodiments, the mass storage device 164 includes a pre-allocated amount of storage space for image data, such as pre-processed image data. In some embodiments, the network interface 165 may be coupled directly to the network 130 or may be coupled to the network 130 through an internet service provider (ISP) 180, or other entity. In some embodiments, the server 160 may include additional modules, such as an image management module 188 (see FIG. 1D). In some embodiments, the image management module 188 may include logic or software to load, read, and convert files including image data. In some embodiments, the image management module 188 may include a converter configured to take incoming scanned image data and automatically convert it for distribution to and viewing within an interface, e.g. a web browser.

Similarly, the client system 170 includes a processing subsystem 102 coupled to a memory subsystem 172, a user interface 171, a storage subsystem 104 and a network interface 112. In some embodiments, the storage subsystem 104 may comprise a pre-allocated space to store image data, such as pre-processed image data received from a server 160. The client 170 may be directly coupled to the network 130 or coupled to the network 130 via an ISP 185, or other entity. The user interface 171 of the client system may include a display 108, a keyboard and a mouse and/or other graphical input device 106. Additionally or alternatively, the user interface 171 may be, for example, a touch screen. In some embodiments, a user interface 171 is rendered by processing subsystem 102 and is provided on display 108 to (i) facilitate the visualization and analysis of imaging data and/or patient data; and/or (ii) to retrieve imaging data, patient information, or other clinical information from a database or a mass storage device 164, such as one available through network 130, based on received user inputs.

In some embodiments, both the server 160 and the client system 170 include caches, i.e. allocated storage spaces within the mass storage device 164 or the storage subsystem 104, respectively. In some embodiments, the caches within the mass storage device 164 or storage subsystem 104 are configured to store image data, such as pre-processed image data derived from a whole slide scan of a biological specimen disposed on a microscope slide.

Figure 1B:
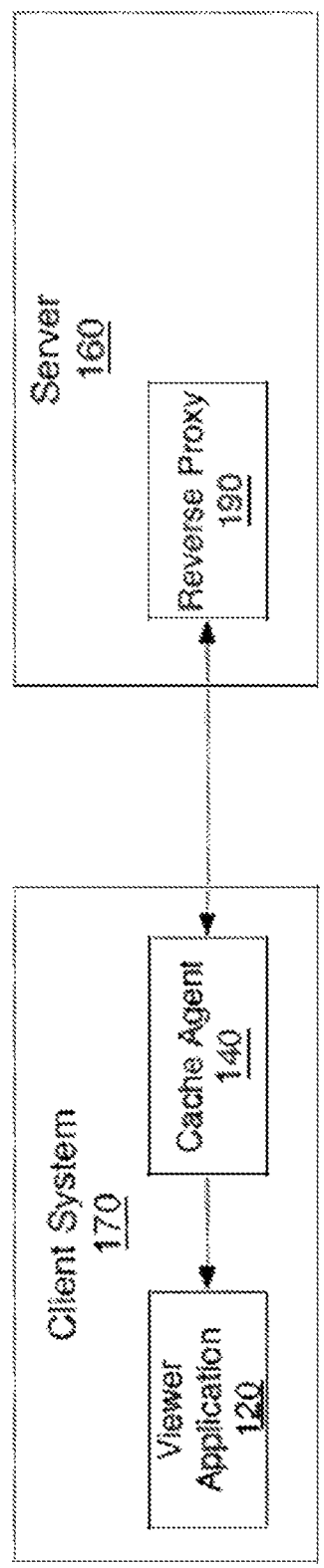
FIG. 1B illustrates a client-server system including a server 160 communicatively coupled to a client system 170, the client system 170 including a viewer application and a caching agent in accordance with some embodiments.
Figure 1C:
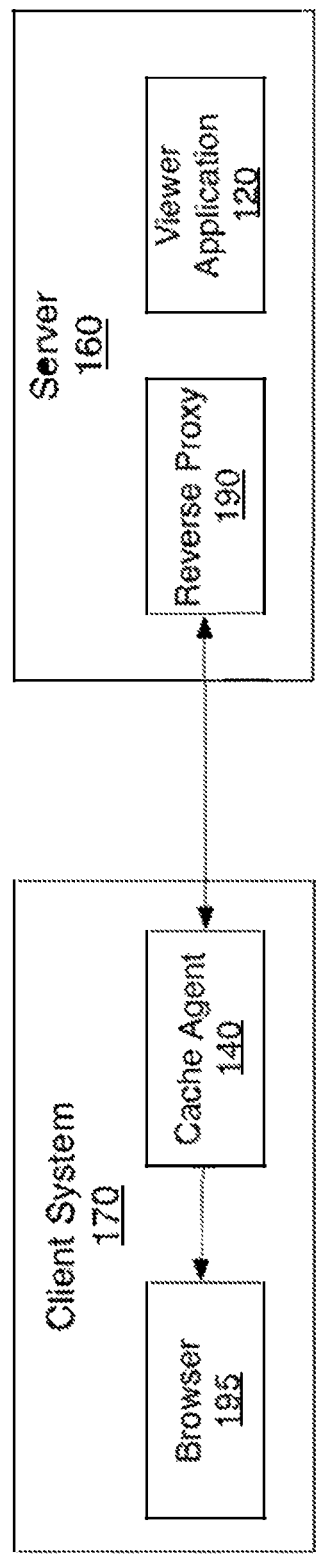
FIG. 1C illustrates a client-server system including a server 160 communicatively coupled to a client system 170, the client system 170 including a browser and a caching agent in accordance with some embodiments.
Figure 1D:
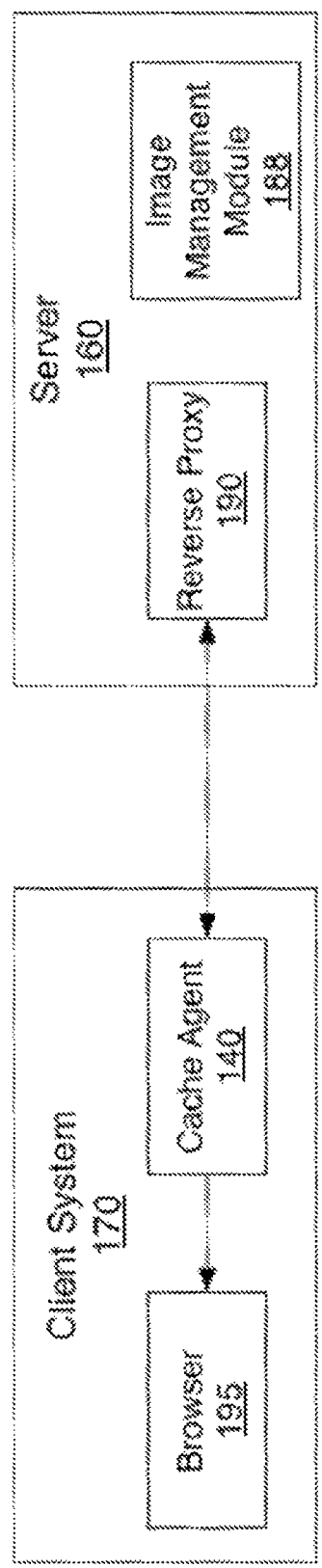
FIG. 1D illustrates a client-server system including a server 160 communicatively coupled to a client system 170, the client system 170 including a browser and a caching agent in accordance with some embodiments.

In some embodiments, software, such as a viewer application 120 and a cache agent 140, are run on a client system 170, and a client interface or client portal (not shown) on the server 160 is used to facilitate communication between the client system 170 and the server 160 (see FIG. 1B). In some embodiments, a viewer application 120 is run remotely on the server 160, and an instance of the viewer application 120 is run within a browser 195 on the client system 170 (see FIG. 7C). In this way, a user (e.g. a pathologist) may interact with elements of the system (e.g. configurable elements) such that image data may be analyzed and/or interpreted (e.g. a histologist or pathologist may select user configurable parameters, such as menu bar tools and/or viewer panels).

Figure 2A:
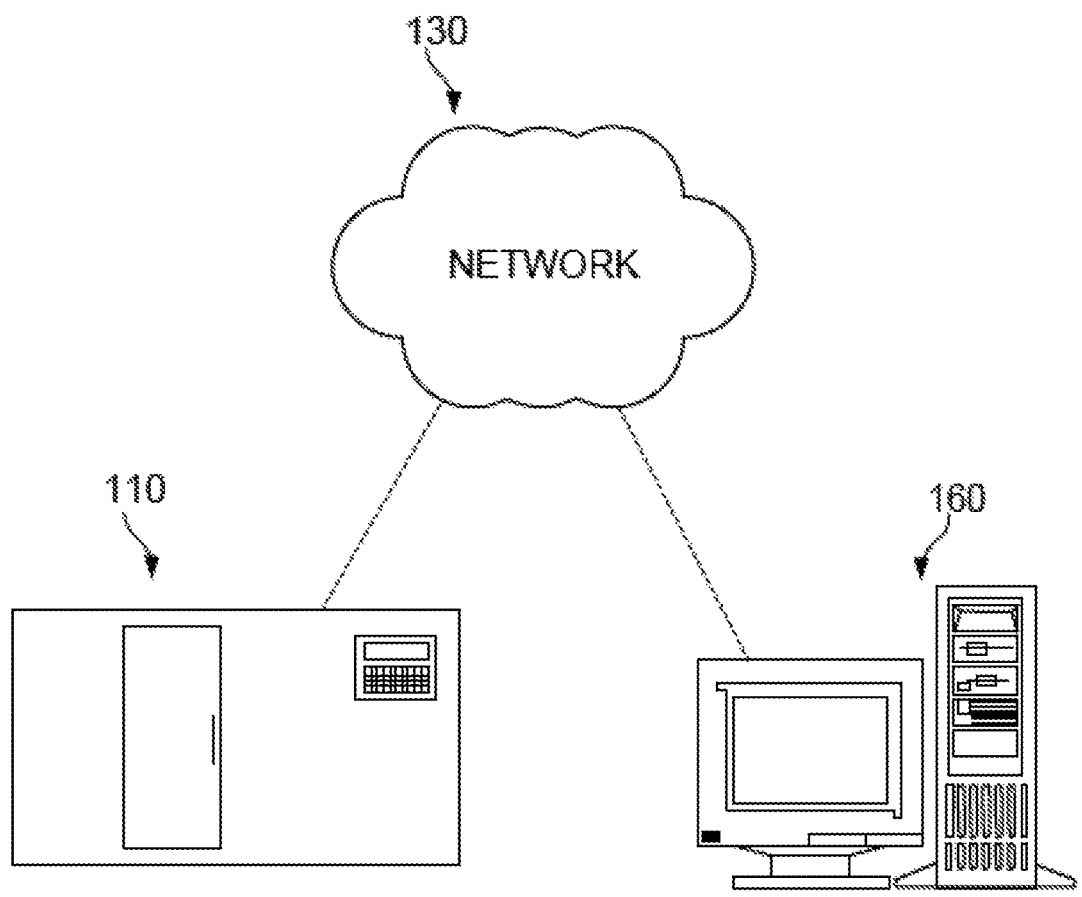
FIG. 2A illustrates a server communicatively coupled to a scanning device in accordance with some embodiments.

In some embodiments, the locally run viewer application 120 or browser 195 transmits requests to an application running on the remote server 160 for the location of image data files. In some embodiments, the location of information data files is stored in one or more URLs. The location of the image data files may be on a remote server, such as in a cache on the remote server or may be within a local cache communicatively coupled to the client system. In either way, the transmitted location information, e.g. URLs, provide the location of the appropriate image data file or image tile files for retrieval. In some embodiments, the URLs provide additional parameters, such as sharpness, contrast, saturation, color, etc. An example of a URL including parameters is as follows: https://localhost/restapp/slide/imageFetcher/1012/116?quality=2&roff=3072,0&rsiz=1536,15 36&imgtype=j pg&brightness=0&contrast=0& saturation=0& sharpness=0&hue=0&color=0,0, 0&transformType=SRGB FIG. 2A illustrates a server 160 (a computer or computing device) communicatively coupled to a scanning device 110. In some embodiments, the server 160 may include software to command the scanning device 110 to perform certain operations using certain user configurable parameters, and to send resulting imaging data acquired to the processing subsystem 161 or the mass storage device 164. In some embodiments, a scanning device 110 may be communicatively coupled to server 160 whereby scanned slides may be transmitted through the network 130 to the server 160 and stored on the mass storage device 164 for later retrieval, e.g. either whole slide images or pre-processed image tiles derived from whole slides images may be stored on the server. For example, image data may be acquired using a scanning device 110 and the scanned image data stored in a file located on a mass storage device 164 or other networked server, whereby the file (including relevant metadata, a patient case identifier, and a user identification) may be later retrieved for visualization and analysis (such as from client 170). In some embodiments, the server 160 and scanning device 110 are separately maintained, e.g. maintained by different organizations, where slides may be scanned by one actor and transmitted to a server 160 under the control of a different actor.

Figure 2B:
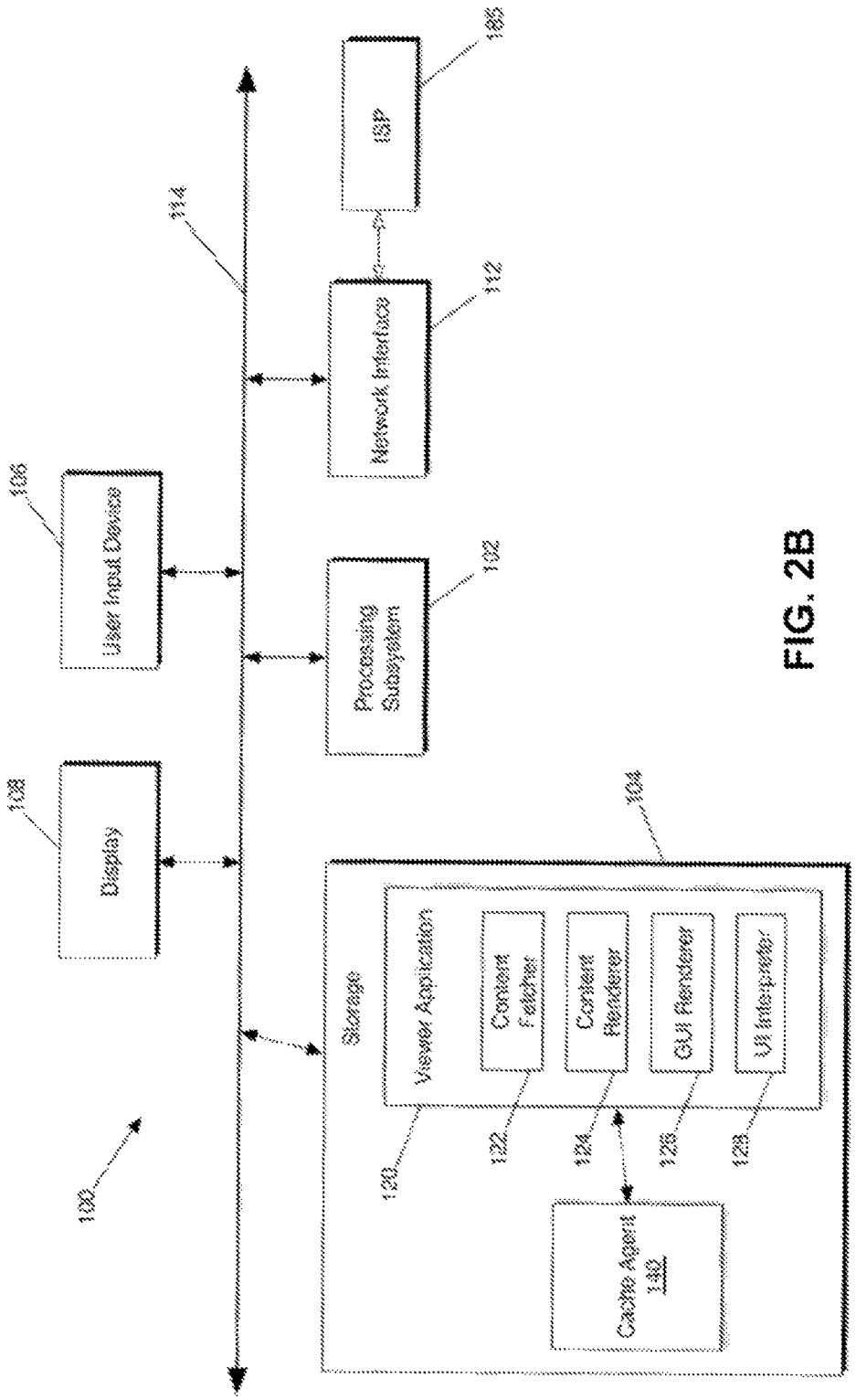
FIG. 2B illustrates a client system including a processing subsystem, a storage subsystem, an output device, and an input device, each of the components communicatively coupled through a bus, a network, or other wired or wireless interconnect, in accordance with some embodiments. The system may include a viewer application which is run locally on the client system and which may access content (e.g. image data) either from a local client cache within the storage subsystem or from a remote server in accordance with some embodiments.
Figure 2C:
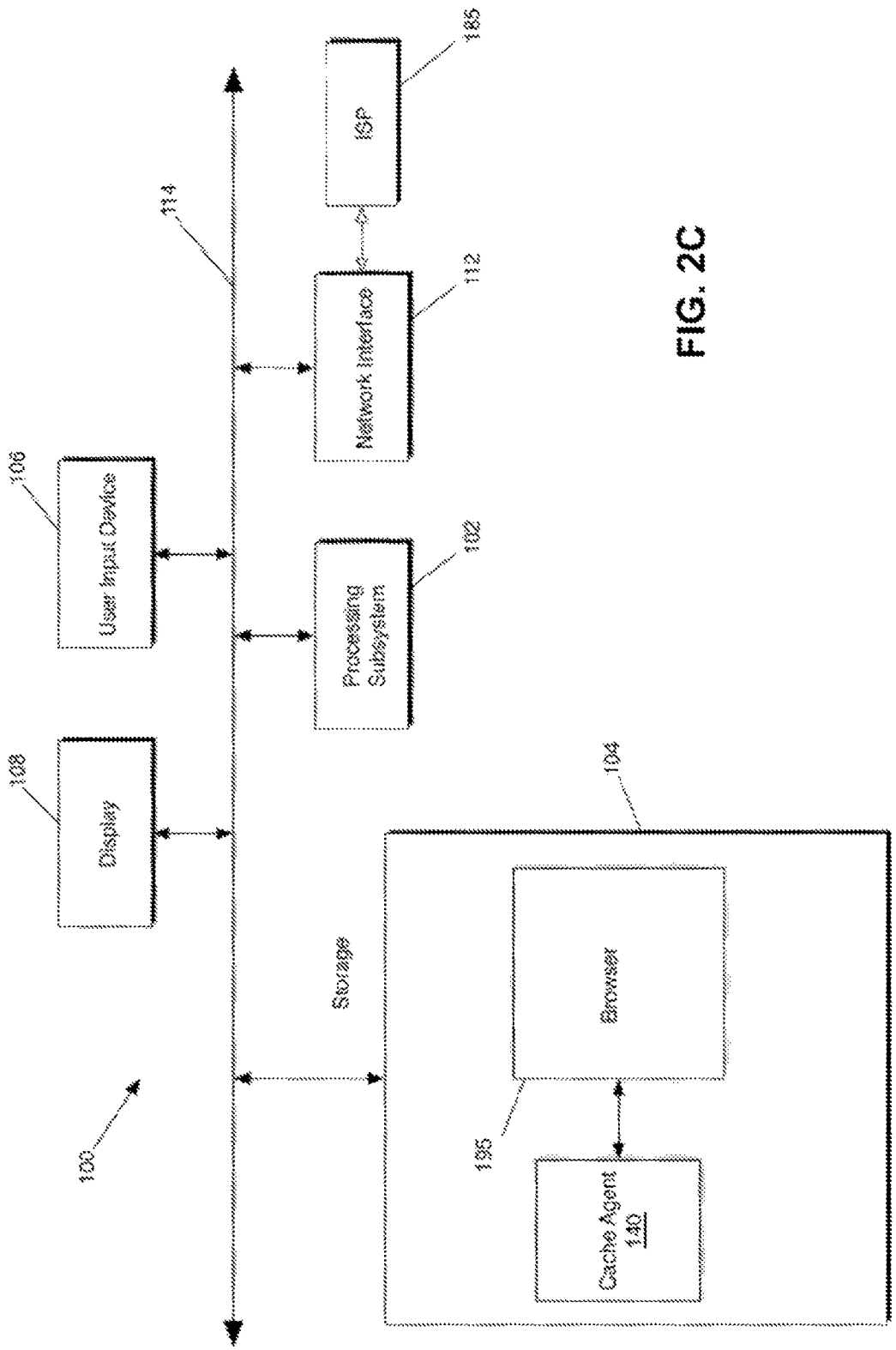
FIG. 2C illustrates a client system including a processing subsystem, a storage subsystem, an output device, and an input device, each of the components communicatively coupled through a bus, a network, or other wired or wireless interconnect, in accordance with some embodiments. The system may include a browser which is run locally on the client system and which may access content (e.g. image data) either from a local client cache within the storage subsystem or from a remote server in accordance with some embodiments.

FIGS. 2B and 2C sets forth a block diagram of a client system 170 according to an embodiment of the present disclosure. Client system 170 can be implemented using any type of user-operable computing device, including desktop computers, laptop computers, tablet computers, handheld devices (e.g., smart phones, media players), and so on. As noted above, client system 170 can include a number of interconnected components such as processing subsystem 102, storage subsystem 104, user input device 106, display 108, and network interface 112 communicating via bus 114, as discussed in more detail below.

Processing subsystem 102 can include a single processor, which can have one or more cores, or multiple processors, each having one or more cores. In some embodiments, processing subsystem 102 can include one or more general-purpose processors (e.g., CPUs), special-purpose processors such as graphics processors (GPUs), digital signal processors, or any combination of these and other types of processors. In some embodiments, some or all processors in processing subsystem can be implemented using customized circuits, such as application specific integrated circuits (ASICs) or field programmable gate arrays (FPGAs). In some embodiments, such integrated circuits execute instructions that are stored on the circuit itself. By way of example only, processing subsystem 102 can execute instructions to receive and process image data stored within a local or networked storage system and display the image data (e.g. display a whole slide scanned image, or a magnified portion of any whole slide scanned image).

Storage subsystem 104 and/or memory subsystem 172 (and their counterparts on server 160) can include various memory units such as a system memory, a read-only memory (ROM), and a permanent storage device. A ROM can store static data and instructions that are needed by processing subsystem 102 and other modules of client system 170. The permanent storage device can be a read-and-write memory device. This permanent storage device can be a non-volatile memory unit that stores instructions and data even when client system 170 is powered down. In some embodiments, a mass-storage device (such as a magnetic or optical disk or flash memory) can be used as a permanent storage device. Other embodiments can use a removable storage device (e.g., a flash drive) as a permanent storage device. The system memory can be a read-and-write memory device or a volatile read-and-write memory, such as dynamic random access memory. The system memory can store some or all of the instructions and data that the processor needs at runtime.

Storage subsystem 104 and/or memory subsystem 172 can include any combination of non-transitory computer readable storage media including semiconductor memory chips of various types (DRAM, SRAM, SDRAM, flash memory, programmable read-only memory) and so on. Magnetic and/or optical disks can also be used. In some embodiments, storage subsystem 104 can include removable storage media that can be readable and/or writeable; examples of such media include compact disc (CD), read-only digital versatile disc (e.g., DVD-ROM, dual-layer DVD-ROM), read-only and recordable Blu-ray® disks, ultra-density optical disks, flash memory cards (e.g., SD cards, mini-SD cards, micro-SD cards, etc.), and so on. In some embodiments, image data and/or patient data can be stored in one or more remote locations, e.g., cloud storage, and synchronized with other the components of client system 170. When the terms "memory" or "a memory" are used herein, they may refer to one or more memories, such as a plurality of memories.

In some embodiments, storage subsystem 104 can store one or more software programs to be executed by processing subsystem 102, such as a viewer application 120 or a cache agent 140. "Software" refers generally to sequences of instructions that, when executed by processing subsystem 102, cause client system 170 to perform various operations, thus defining one or more specific machine implementations that execute and perform the operations of the software programs. Thus, "software" can also include firmware or embedded applications or any other type of instructions readable and executable by processing subsystem 102. Software can be implemented as a single program or a collection of separate programs or program modules that interact as desired. In some embodiments, programs and/or data can be stored in non-volatile storage and copied in whole or in part to volatile working memory during program execution. From storage subsystem 104, processing subsystem 102 can retrieve program instructions to execute and data to process in order to execute various operations including operations described below.

A user interface 171 can be provided to a display device 108, and/or and one or more other user output devices (not shown). The user interface 171 may include, for example, visualizations and other representations, the representations including images derived from scans of stained biological samples (e.g. samples stained for the presence of one or more biomarkers or stained with hematoxylin and eosin), menu bars, drop-down menus, and/or panels. Input devices 106 can include any device via which a user can provide signals to client system 170; client system 170 can interpret the signals as indicative of particular user requests or information. In some embodiments, input devices 106 can include any or all of a keyboard touch pad, touch screen (e.g., a touch-sensitive overlay on a display surface of display 108), mouse or other pointing device, scroll wheel, click wheel, dial, button, switch, keypad, microphone, and so on.

Display 108 can display visualizations (e.g. representations including image data, viewer panels to convey information to a user, or contextual menus which provide user selectable configuration options, etc.) generated by client system 170 and can include various image generation technologies, e.g., a cathode ray tube (CRT), liquid crystal display (LCD), light-emitting diode (LED) including organic light-emitting diodes (OLED), projection system, or the like, together with supporting electronics (e.g., digital-to-analog or analog-to-digital converters, signal processors, or the like). Some embodiments can include a device such as a touchscreen that function as both input and output device. In some embodiments, other user output devices can be provided in addition to or instead of display 108.

In some embodiments, the user interface can provide a graphical user interface (such as through a browser or in a viewer application on the client system 170), in which visible image elements in certain areas of display 108 are defined as active elements, interactive elements, or control elements that the user selects using user input devices 106. For example, the user can manipulate a user input device 106 to position an on-screen cursor or pointer over the control element, then "click" a button to indicate the selection, with the selection sending signals to perform a designated action or routine. For example, the user can manipulate the user input device 106 to select an icon within the user interface (such as one in a viewer panel, in a menu bar, or within a drop down menu), which would effectuate the initiation of an operation or selection of a tool. In some embodiments, the user may manipulate the user input device 106 to select certain images within a patient case, to zoom in on an image, to pan across a displayed image (i.e. to change visual fields), tilt an image, rotate an image, etc. In some embodiments, the user can manipulate the user input device 106 so as to interact with dropdown menus to select one or more panels, including interactive panels.

Additionally or alternatively, the user can touch the control element (e.g., with a finger or stylus) on a touchscreen device. In some embodiments, the user can speak one or more words associated with the control element (the word can be, e.g., a label on the element or a function associated with the element). In some embodiments, user gestures on a touch-sensitive device can be recognized and interpreted as input commands; these gestures can be, but need not be, associated with any particular area on display 108. Other user interfaces can also be implemented.

Network interface 112 may provide data communication capability for client system 170. In some embodiments, network interface 112 can include radio frequency (RF) transceiver components for accessing wireless voice and/or data networks (e.g., using cellular telephone technology, advanced data network technology such as 3G, 4G or EDGE, 5G, WiFi (IEEE 802.11 family standards), or other mobile communication technologies, or any combination thereof, GPS receiver components, and/or other components. In some embodiments, network interface 112 can provide wired network connectivity (e.g., Ethernet) in addition to or instead of a wireless interface. Network interface 112 can be implemented using a combination of hardware (e.g., antennas, modulators/demodulators, encoders/decoders, and other analog and/or digital signal processing circuits) and software components.

Bus 114 can include various system, peripheral, and chipset buses that communicatively connect the numerous components of client system 170. For example, bus 114 can communicatively couple processing subsystem 102 with storage subsystem 104. Bus 114 can also connect to input devices 106 and display 108. Bus 114 can also couple processing subsystem 102 to a network through network interface 112. In this manner, client system 170 can be connected to a network 130 of multiple computer systems (e.g., a local area network (LAN), a wide area network (WAN), an Intranet, or a network of networks, such as the Internet. The skilled artisan will appreciate that additional components may be connected to bus 114, such as a scanning device, a scanning device, a tissue processing system, etc.

Some embodiments include electronic components, such as microprocessors, storage and memory that store computer program instructions in a computer readable storage medium. Many of the features described herein may be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter.

Through suitable programming, processing subsystem 102 can provide various functionalities for client system 170. For example, processing subsystem 102 can execute a browser which communications with a remote server 160 and which facilitates the review and interpretation of scanned images of biological samples. The browser may be configured to run an instance of a remote application, such as a viewer application) and can provide various functionality such as the ability to select user configurable options or user selectable panels, or the ability to control navigation and annotate the images (see FIG. 2C). By way of another example, processing subsystem 102 can execute a viewer application 120 (i.e. one run locally such as in FIG. 2B) having a user interface which facilitates the review and interpretation of scanned images of biological samples. The viewer application 120 can provide various functionality such as the ability to select user configurable options or user selectable panels, or the ability to control navigation and annotate the images.

In some embodiments, the viewer application 120 incorporates various interoperating modules (e.g., blocks of code) that, when executed by one or more processors within the processing subsystem 102, implement aspects of the interface operation. For example, the viewer application 120 can include a content fetcher 122 (e.g. one adapted to retrieve URLs or image data from server 160 through the network 130), a content renderer 124 (e.g. to decipher received image data or patient data), a GUI renderer 126 (e.g. to continually generate representations and visualizations based on user selections and commands and based on image data received by the content fetcher 122), and a UI interpreter 128 (e.g. to interpret user selections and commands, such as a pan command; a zoom command; and a select command).

With reference to FIG. 2B, in some embodiments, the viewer application 120 is configured to communicate with the server 160, e.g. configured to send requests for image location information, e.g. URLs, to the server 160 and to receive such image location information from the server 160. In some embodiments, the viewer application 120 may communicate with the cache agent 140 to access image data in the client cache based on the received location information, such as in one or more URLs. In some embodiments, the viewer application 120 (or the cache agent 140) may be redirected to a server (or a reverse proxy) for the retrieval of image data if the client cache no longer includes the requested image data in cache (e.g. the image data may have been automatically removed from cache based on user-established criteria).

With reference to FIG. 2C, in some embodiments, a viewer application 120 is instead run on the server 160 (such as through network 130) and a browser 195 is run on the client system 170, whereby the browser 195 may remotely run an instance of the viewer application, or where the browser may communicate with a viewer application or other software running on the remote server 160. In either case, the browser is configured to send requests for image data locations, such as URLs, to the server 160. Based on the received file location information, in some embodiments, the browser 195 may communicate with the cache agent 140 to access image data in the client cache based on the received image location information. In some embodiments, the browser 195 (or the cache agent 140) may be redirected to a server (or a reverse proxy) for the retrieval of image data if the client cache no longer includes the requested image data in cache (e.g. the image data may have been automatically removed from cache based on user-established criteria).

In some embodiments, the cache agent 140 may be communicatively coupled to the viewer application 120 or browser 195 of client system 170 and also communicatively coupled to server 160. In some embodiments, the cache agent 140 is separate from a locally run viewer application 120 or browser 195 and, in some embodiments, is always running, i.e. it runs even after a viewer application 120 or browser 195 is closed. In some embodiments, the cache agent 140 communicates directly with the server 160, such through an HTTP protocol and, in and of itself, may be considered as an HTTP server running on the client system 170.

In some embodiments, the cache agent 140 is a client-side cache management application, configured to manage image data (e.g. or portions of scanned images, such as image tiles as described herein) and manage the caching of image data or image tiles according to various events or pre-established user criteria. In some embodiments, the cache agent 140, when running, may receive requests from a viewer application 120 or browser 195, such as requests to receive image data, including pre-processed image data, based on location information received from server 160. By way of example, the server 160 may be configured to automatically send newly received or scanned image data to client system 170 (such as after pre-processing the scanned image data) and the cache agent 140 may manage the communication with server 160 and also manage the receipt of the image data. In some embodiments, the cache agent 140 is configured to manage the client cache itself, e.g. to determine which image data sets to retain and which to remove, such as based on pre-established user criteria (described further herein). In some embodiments, the cache agent 140 is configured determine whether to retain or remove image data sets that have been previously visualized and/or analyzed. In some embodiments, the client cache is a pre-allocated amount of storage space within storage subsystem 104 of the client system 170.

In some embodiments, the cache agent 140 may optionally send data to the server indicating that certain sets of image data (or entire patient cases) have been reviewed by the user and/or that the already removed image data has been or will be removed from the cache (such as a set date according to user configured cache expiration criteria). In some embodiments, the cache agent 140 provides no data to the server 160.

In some embodiments, the cache agent 140 may be configured to facilitate the delivery of image data to a browser 195 or viewer application 120. For example, the viewer application 120 may request a location of image data that is needed based on user inputs and may request this information from server 160 (e.g. it may request a URL to image data), and the cache agent 140 may function to retrieve the image data from the client cache, provided that such image data was retained by the cache agent 140.

Populating a Client Cache with Image Data

Figure 3:
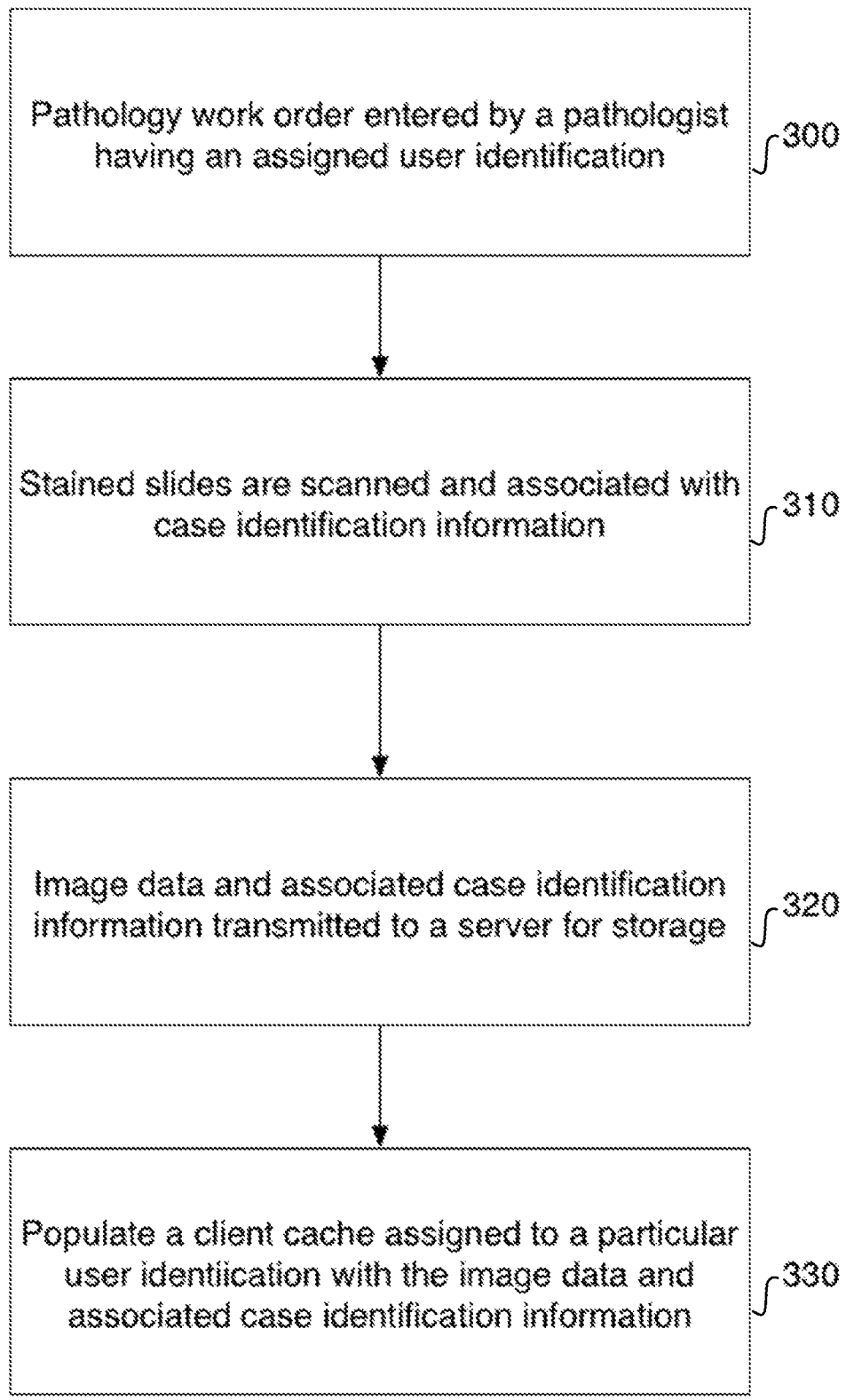
FIG. 3 sets forth a flowchart providing the general steps creating a patient case and associating that created patient case with scanned image data and a pathologist user identification in accordance with some embodiments.

FIG. 3 sets forth a flow chart illustrating the acquisition of image data from stained biological samples. In a first step (300), a pathology work order is created and entered by a pathologist. In some embodiments, the pathologist has an assigned user identification. As such, any work order created by the pathologist can be traced back to the pathologist's user identification.

Next, stained slides (such as those prepared by a histopathologist) are scanned) (step 310). In some embodiments, image data is acquired from a scanning device (such as the VENTANA DP 200 scanner, available from Ventana Medical Systems, Inc., Tucson, AZ) and the image data may be stored in a database, such as a networked database or on a mass storage device 164, for later visualization and analysis.

In some embodiments, the scanning device, generates a high resolution image of each slide for subsequent display and viewing. In some embodiments, the scanning device, generates high resolution images of each slide at multiple magnification levels, e.g. 20× or 40×. In some embodiments, the image data for all of the slides relating to the specimen and the clinical details for the specimen may be stored in a database, together with metadata about the virtual slide. The scanned slides are associated with patient case identification information (and pathologist user identification), including the metadata. In some embodiments, the scanned image data is stored in a first file format, such as an uncompressed image file format. In some embodiments, the scanned image data, e.g. a scan of a whole slide image, is stored as a DICOM file, a BIF file, or a TIFF file. In some embodiments, the DICOM file or BIF file may include RAW image data or other uncompressed image data at multiple magnification levels.

Subsequently, the image data from the scanning device 110 and associated patient case identification information are transmitted to a server 160 for storage (e.g. transmitted to server 160 and stored within mass storage device 164) (step 320 of FIG. 3, step 1000 of FIG. 10). In some embodiments, the scanned image data is stored as individual files, i.e. a single file is stored on the server 160, the single file representing a scan of a whole slide image in a first file format. In some embodiments, upon a user request, image tiles are generated and transmitted to a client system.

Figure 10:
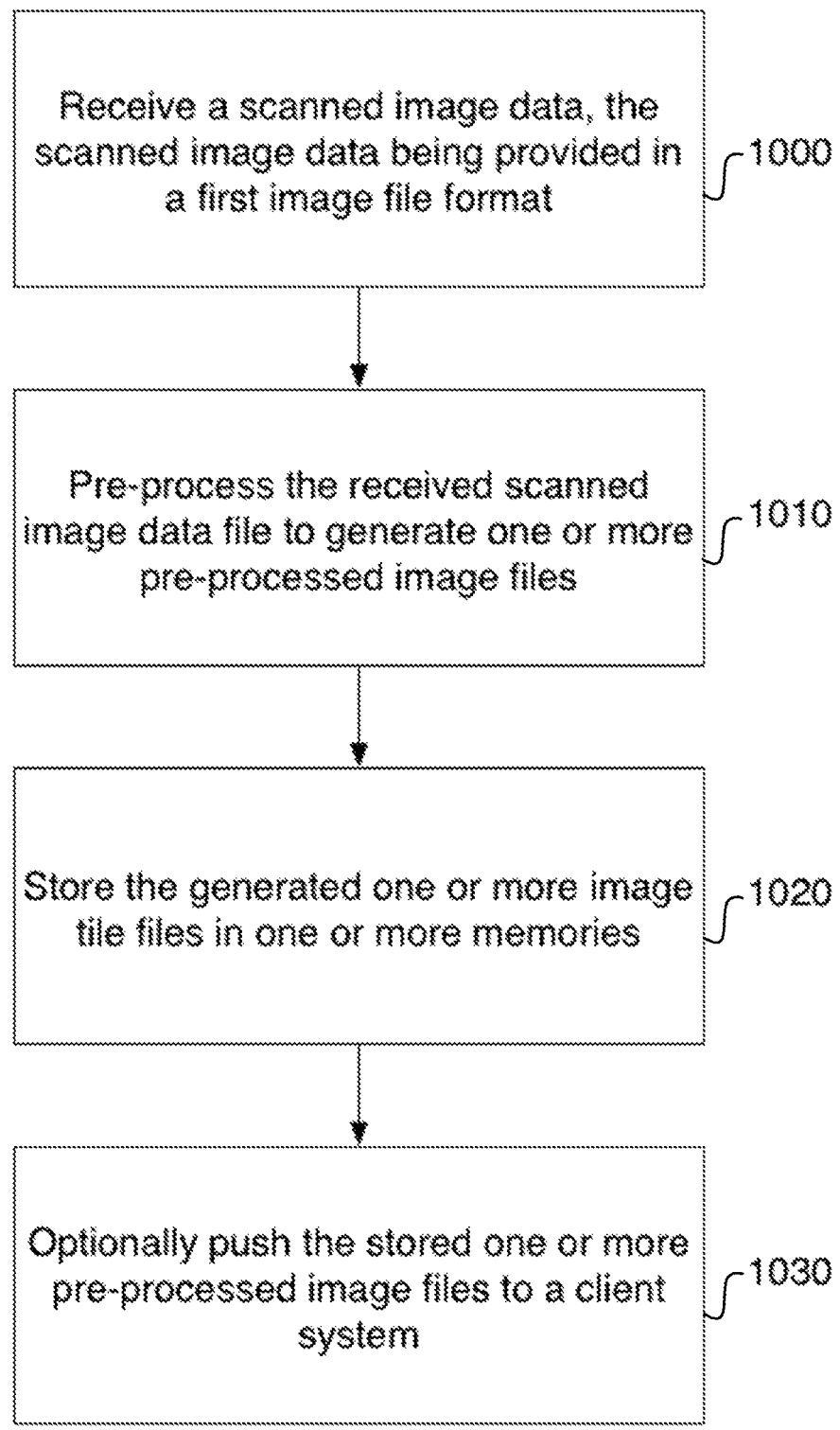
FIG. 10 sets forth a flowchart providing the steps of pre-processing image data on a server, such as pre-processing image data received in an input file format to a destination file format in accordance with some embodiments.

In some embodiments, the scanned image data is automatically pre-processed on server 160, such as with an image management module 188, after it is received from the scanning device 110 (see FIG. 10, step 1010). In some embodiments, the image management module 188 includes logic or software to load received image data, read the received data, convert the received image data from a first format to a second format, and/or or perform other image processing operations, such as extracting portions of the received image data and outputting the extracted portions to separate files.

In some embodiments, the scanned image data is pre-processed such that a single image file in a first format (e.g. an input file format) is converted to a single image file having a second format, whereby the first image format and the second image format are different. For example, a whole slide image in a first format may be converted to a whole slide image in a second format. In some embodiments, the second image file format is a destination file format. In some embodiments, the destination file format is one that is pre-selected for use on a client system 170, or one that is compatible with a browser application (such as a standard web browser application running on a personal computer). In some embodiments, the second image file format is a compressed file format including, but not limited to, JPEG, JPEG 2000, and PNG. By way of example, a single DICOM, BIF, or TIFF image file may be converted to a single compressed image file, e.g. a single JPEG file.

Additionally or alternatively, where a single DICOM or BIF image file comprises image data pertaining to multiple scanning magnification levels, a single compressed image file may be generated for each magnification level. For example, if a BIF image comprises whole slide image data at a 20× magnification level and whole slide image data at a 40× magnification level, then two compressed image files (e.g. JPEG files) may be generated, one at 20× and the other at 40× and both being whole slide images. In some embodiments, these compressed image files may be transmitted to a user upon request (e.g. upon a request, the compressed image file at a certain magnification may be broken down into individual a plurality of tiles and transmitted in real-time to the user).

In some embodiments, the scanned image data is pre-processed (step 1010 of FIG. 10) such that a single image file in a first format is split into a plurality of pre-processed image files, where each of the plurality of pre-processed image files may have either the same or different file format as compared with the first file format. For example, a single image file in a first file format, e.g. a TIFF file format, may be split into a plurality of pre-processed image files, e.g. 500 pre-processed image files or more, each having the TIFF file format or a different file format. By way of another example, the TIFF image file may be split into a plurality of pre-processed image files having the TIFF format, e.g., a single TIFF file may be split into 500 or more pre-processed image files in the TIFF format.

Additionally or alternatively, and again following the above example, the TIFF image file may be split into a plurality of pre-processed image files having a different file format, such as an compressed image file format, including JPEG, JPEG2000, and PNG. In these embodiments, the TIFF image file may be first converted to the second file format (e.g. JPEG) and then split into a plurality of pre-processed JPEG image files; or, the TIFF image file may first be split into a plurality of pre-processed image files having the TIFF file format and then each individually converted to JPEG file. In either case, the result is a plurality of pre-processed image files having a different file format, such as a destination file format, including a format compatible with a web browser.

In some embodiments, pre-processing may generate multiple sets of pre-processed image files, and each individual set of image pre-processed image files may include a plurality of image tile files. For example, and as noted above, a whole slide scan in DICOM format or BIF format may include image data corresponding to several magnification levels, e.g. 1×, 20×, and 40×. In some embodiments, a plurality of image tile files may be generated for each magnification level within the original whole slide scan. For example, a first set of generated pre-processed image files may include a plurality of image tile files relating to a 20× magnification, while a second set of generated pre-processed image files may include a plurality of image tile files relating to a 40× magnification.

In some embodiments, after the pre-processed image files are generated, they are stored in one or more memories (step 1020) including, but not limited to, volatile and non-volatile memories. In some embodiments, the pre-processed image files are stored in a pre-allocated storage space within the mass storage device 164 communicatively coupled to server 160. In some embodiments, the pre-processed image files each comprise a unique file name. In some embodiments, the unique file name includes the coordinates of a position of a tile image derived from a whole slide image. In this way, if a user requests tiles at coordinates (x1, y1), (x2, y1), and (x3, y1), then pre-processed tile image files corresponding to each of those locations may easily be retrieved based on the unique file names attributed to each image tile file.

In some embodiments, the pre-processed image files may then be transmitted to a client system 170. In some embodiments, the pre-processed image files may be transmitted to the client system 170 upon receipt of a user input requiring the fetching of certain image data (see, e.g. step 710 in FIG. 710), e.g. transmitted in real-time upon a user input requiring specific image tiles. In some embodiments, the pre-processed image files may be pushed out to the client system 170 as after pre-processing of the images is completed (e.g. after the completion of steps 1000 through 1020). For example, the pre-processed image files may be delivered to a cache agent 140 running on the client system 170 such that image data may be retrieved locally from a storage subsystem of the client system upon receiving a user input requiring specific image tiles as described herein (see step 330 of FIG. 3; see also FIGS. 4A and 7). In some embodiments, the data is pushed out to a client system which has been assigned a particular patient case identification and to a system utilized by a pathologist having a particular user identification. Said another way, in some embodiments, the image data is pushed out to a particular pathologist's computer to whom the patient case is assigned.

Figure 4A:
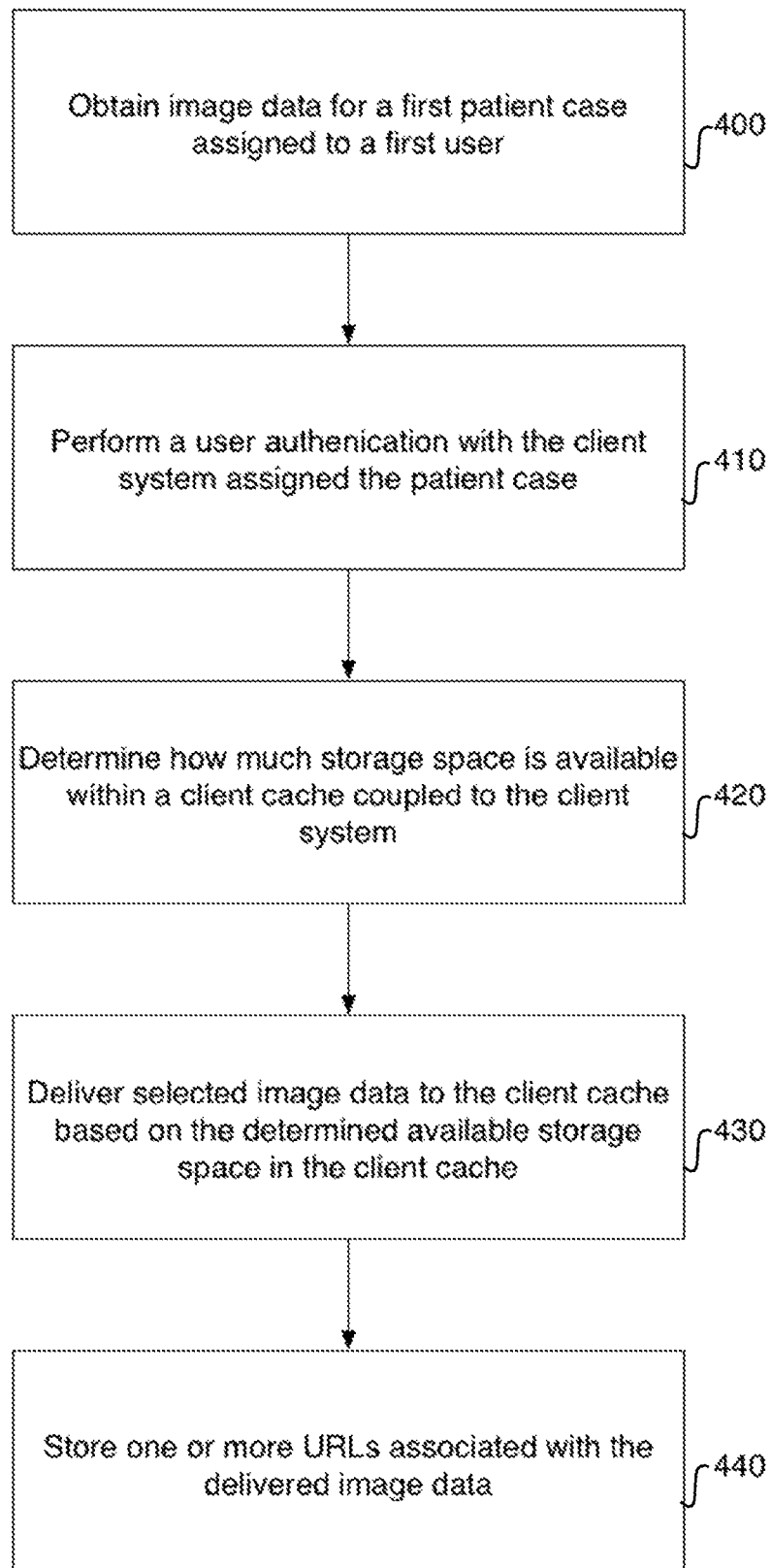
FIG. 4A sets forth a flowchart providing the general steps of delivering content (e.g. image data or portions thereof) to a client cache managed by a cache agent running on a client system in accordance with some embodiments.

The steps of populating a client cache on a client system 170 with newly received (i.e. newly generated image data) is set forth in FIG. 4A. In some embodiments, if data has not already been accessed from the scanning device 110 of a computer system coupled to the scanning device, the server 160 accesses the newly generated image data which has been correlated with a specific user identification (step 400). In some embodiments, the accessed scanned image data (such as in an input file format) may be pre-processed prior to being pushed to the cache agent 140 as described above.

Figure 4B:
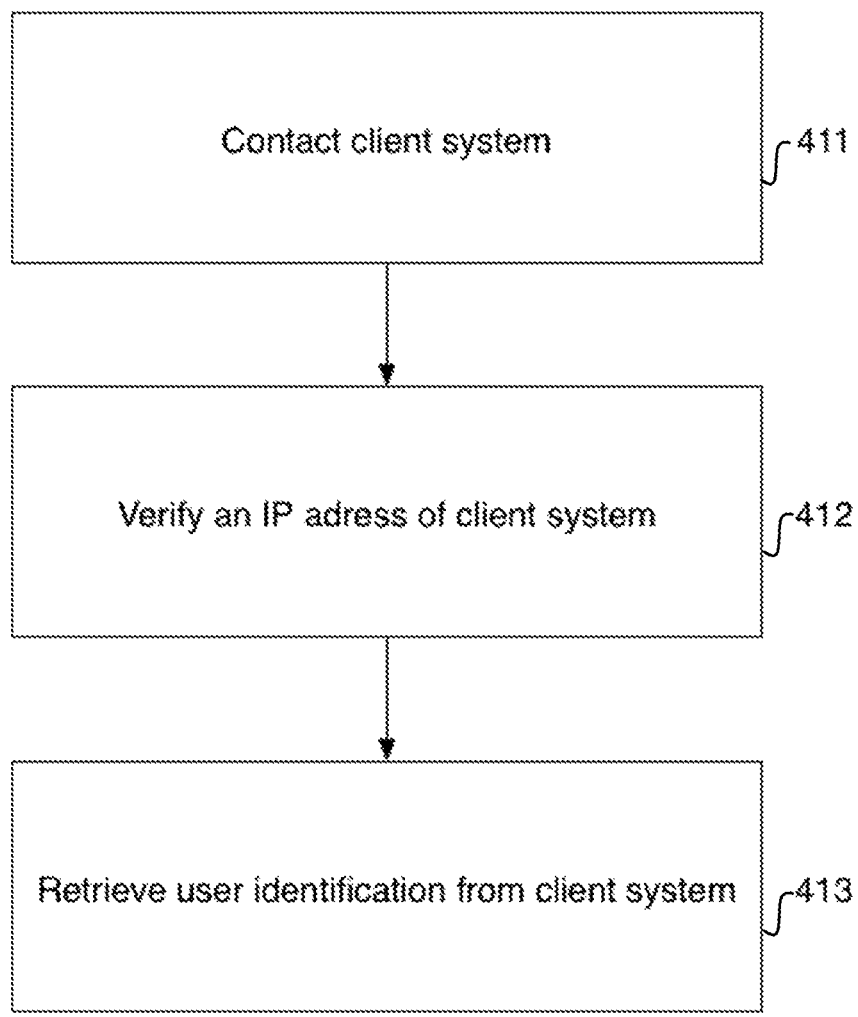
FIG. 4B sets forth a flowchart providing the general steps of performing an authentication between a client system and a remote server, including client systems running a cache agent in accordance with some embodiments.

Next, the server 160 performs an authentication with the client system 170 (step 410) to ensure that the client system 170 is running a cache agent 140 (such that a managed client cache may be populated) and to ensure that the correct information is being delivered to the correct computer and correct user (i.e. the correct pathologist for visualization and analysis). In some embodiments, the server 160 transmits an authentication request to the client system 170 (see step 411 of FIG. 4B). Following the authentication request, in some embodiments, the client system 170 transmits its internet protocol (IP) address to the sever 160 (step 412 of FIG. 4B), which the server 160 verifies as belonging to the correct client system 170. Next, the sever 160 requests and the client system 170 transmits user identification data (step 413 of FIG. 4B). In some embodiments, authentication is completed once the correct system and user are both identified. Of course, other identification data may be used for authentication purposes.

Figure 9:
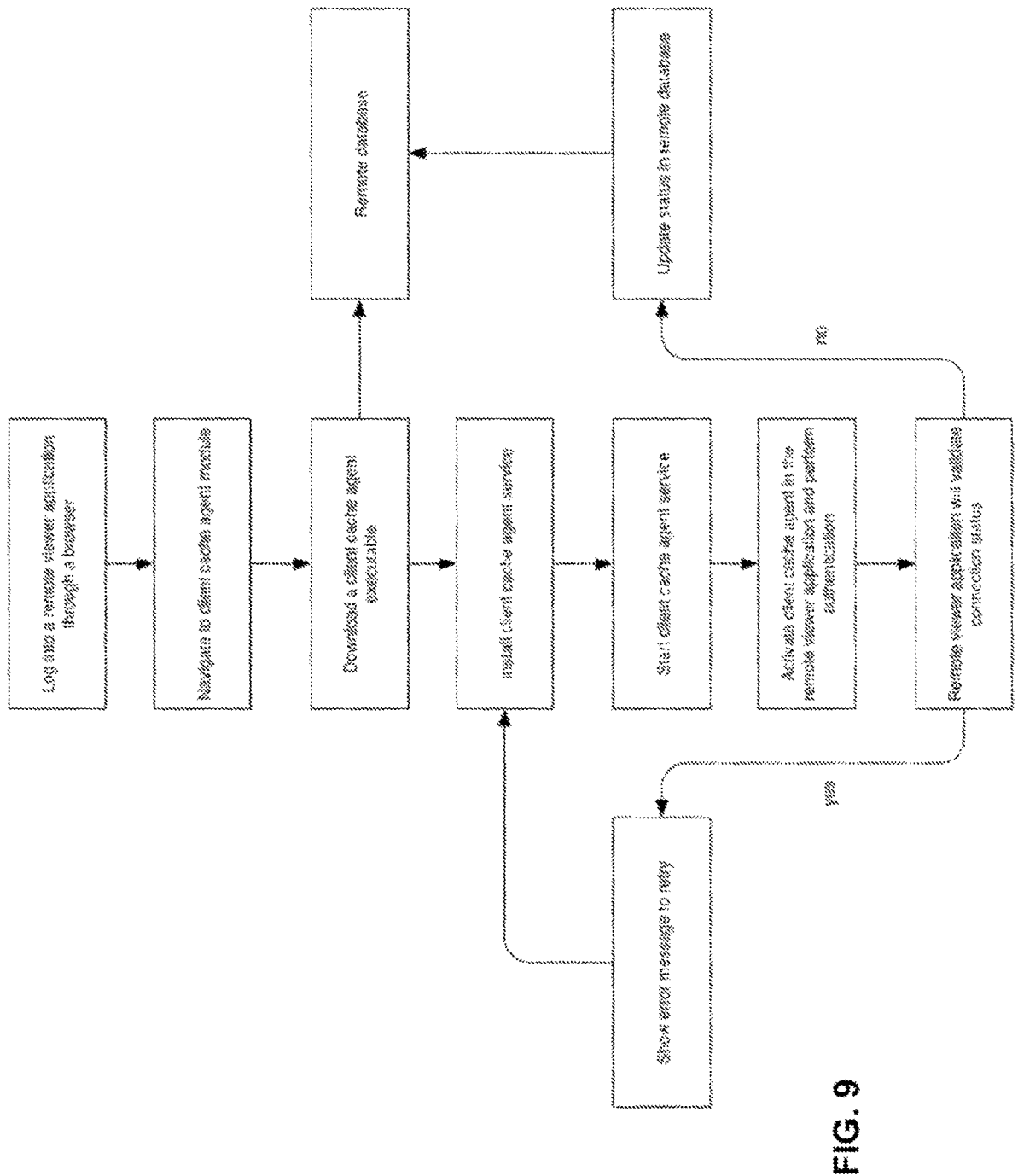
FIG. 9 sets forth a flowchart providing the steps of installing a client cache agent on a client system in accordance with some embodiments.

In some embodiments, authentication is performed only once, e.g. after the installation of a cache agent 140 on the client system 170 (see, for example, FIG. 9). In these embodiments, an authentication is still performed but rather than confirming user identification credentials and/or the IP address of the client system 170, the authentication merely confirms that the cache agent is still running on the system.

Following authentication, in some embodiments, the server 160 transmits all image data available to the client system 170. In these embodiments, the cache agent 140 is provided the task of clearing space within the client cache coupled to the client system 170 to store all of the newly received image data. For example, if 10 GB of pre-processed image tile files are to be transferred from the server 160 to the client system 170, but only 5 GB of space is available within the client cache, the cache agent 140 will remove 5 GB of existing image data within the client cache to make room for all of the image data being received by the server. The maintenance of available cache space may be determined based on pre-established criteria, such as described herein.

In some embodiments, only portions of all of the image data available are pushed to the client system 170. For example, and in some embodiments, the sever 160 transmits portions of the accessed image data based on whether a user has already reviewed the data. For example, if certain image data was previously delivered but not reviewed by a user prior to a cache expiration date for that previously delivered image data (described herein), that image data (or portions thereof) may be again delivered to the client cache.

In some embodiments, the server 160 transmits those portions of the image data based on predetermined selection criteria. In some embodiments, the server 160 transmits those portions of the image data that are the oldest. For example, if within the 10 GB of image data available to be pushed to the client system 170 there exists image scans from a first scan date, and image scans from a second scan date, and the first scan date precedes the second scan date, the older image scans from the first scan date may be those selected to be transmitted to the client cache. In some embodiments, the server 160 transmits those portions of the image data that are flagged with an indicia, e.g. those whose review must be commenced out-of-order, those having a higher priority, those images belonging to a case that is already in-review (e.g. deliver new scans of new images for a case already being reviewed), etc.

In some embodiments, the server 160 may perform a determination of how much storage space is available within the client cache coupled to the client system 170 (step 420). In some embodiments, the cache agent 140 running on the client system 170 may send a value representing the amount of pre-allocated storage space within the client cache that is available at the time of the request by the server 160. In some embodiments, the server utilizes the transmitted value from the cache agent 140 (i.e. the value representing the amount of storage space available within the client cache) to make a determination as to how much of the available scanned image data received by server 160 may be transmitted to the client cache. In some embodiments, the server 160 selects portions of the image data for delivery to the client cache (step 430) based on the available space in the client cache.

For example, if the image data available for delivery on the server comprises 10 GB of information and only 5 GB of storage space is available within the client cache, the server 160 may make a determination of which portions of the image data to send, i.e. which patient cases, images, pre-processed images or portions thereof, image tiles, etc. to send to the client system 170 based on the available space within the client cache. In some embodiments, the portions of the image data selected for delivery may be from a single patient case or from multiple patient cases. For example, a series of pre-processed image tiles may be delivered pertaining to a first patient case, and another series of pre-processed image files may be delivered from a second patient case. In some embodiments, the portions of image data selected for delivery may be pre-processed image tiles derived from certain magnifications within the scanned image file (e.g. deliver 40× magnification pre-processed image tiles only, and not three different sets of pre-processed image tiles at different magnifications given space constraints within the client cache). In some embodiments, the entire free available space of the client cache is populated with available image data from the server 160.

After at least a portion of the available image data residing on the server is delivered to the client cache, one or more URLs providing the location of the stored image data are generated and stored on the sever 160 (these URLs may be later retrieved by the viewer application, such as by a viewer application running on the server or an instance of the viewer application loaded within a browser on the client system). In some embodiments, the URLs comprise various image parameters, including brightness, sharpness, contrast, color, etc. An example of a suitable URL is as follows: https://localhost/restapp/slide/imageFetcher/1012/ 116?quality=2&roff=3072,0&rsiz=1536,15 36&imgtype=j pg&brightness=0&contrast=0&saturation=0&sharpness= 0&hue=0&color=0,0, 0&transformType=SRGB. In some embodiments, a portion of the URL may be with a client agent URL if the image is to be fetched from a client cache. In some embodiments, the URLs may be retrieved by a client system 170, such as a viewer application 120 and/or a cache agent 140 running on the client system 170, such that image data, such as image data present within the client cache, may be retrieved for visualization and/or analysis.

Figure 5:
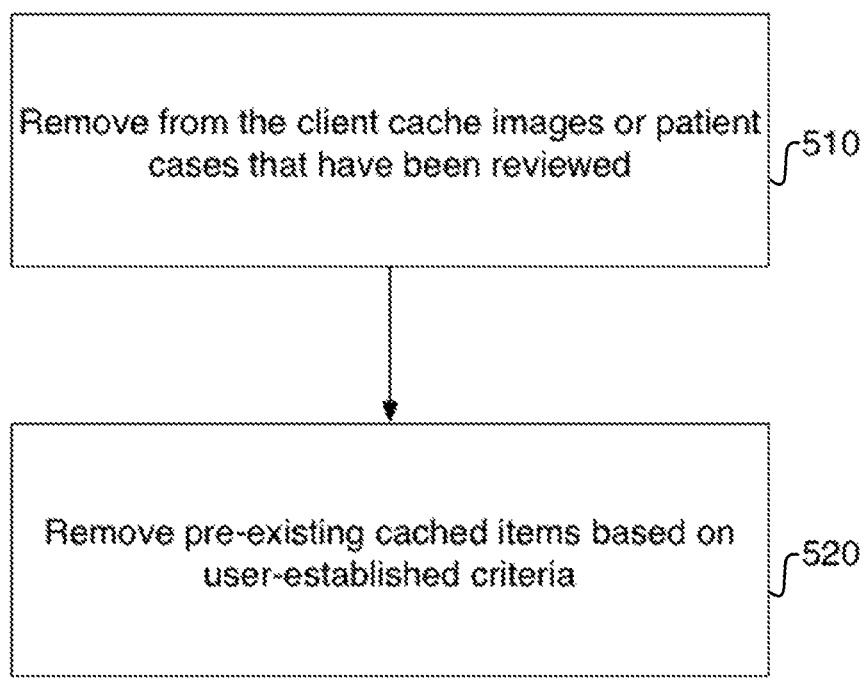
FIG. 5 sets forth a flowchart illustrating the general steps of maintaining a client cache, such as facilitated by a cache agent running on a client system in accordance with some embodiments.
Figure 6:
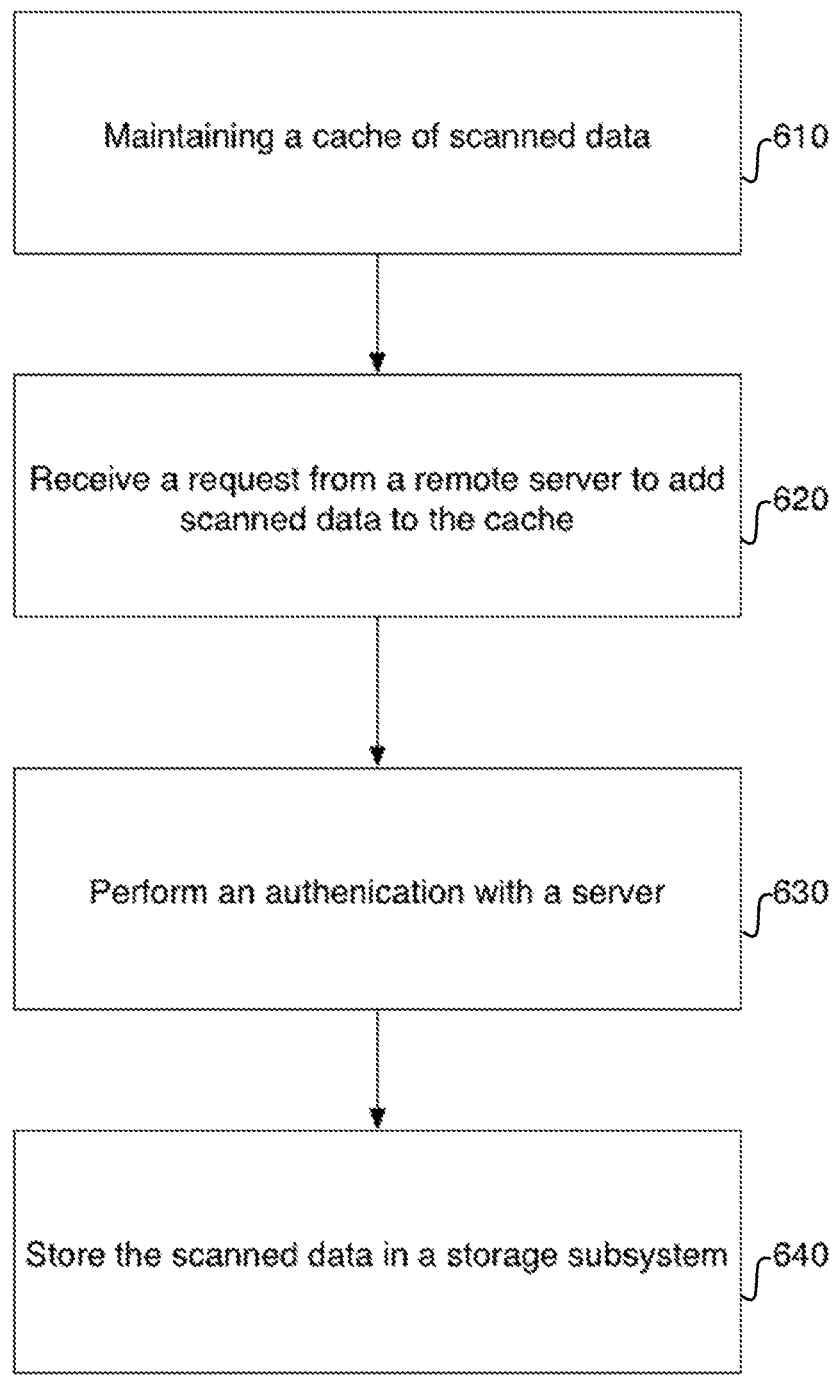
FIG. 6 sets forth a flowchart illustrating the general steps of receiving image data from a remote server, such as data pushed from a remote server into a client cache managed by a cache agent in accordance with some embodiments.

In some embodiments, the cache agent 140 manages the image data stored within the client cache residing on a storage subsystem 104 of client system 170 (see 610 of FIG. 6). In some embodiments, the cache agent 140 maintains the client cache periodically, e.g. at fixed times or at fixed intervals. In some embodiments, the cache agent 140 maintains the client cache on an as needed basis. In some embodiments, the cache agent 140 removes from the client cache those cached image data sets that have already been reviewed by a user (see step 510 FIG. 5). For example, the cache agent 140 may remove cached image data pertaining to a specific set of slides that have already been reviewed. By way of another example, the cache agent 140 may be configured to remove entire patient cases that have already been reviewed by the user.

In some embodiments, the cache agent 140 may be configured to remove cached image data based on pre-existing and user-established criteria (see step 520). For example, cached image data may be removed if a user fails to review the cached image data in a pre-established time period. By way of another example, the cached data itself may have an expiration period, regardless of whether the image data has been reviewed by a user or not (e.g. a set period of 3 days or 1 week or 1 month). By way of yet another example, the cached data may be removed by the cache agent 140 if a patient case has been reassigned from one user to another. By way of yet another example, the cached data may be removed once a certain storage space threshold is met, e.g. if only a certain amount of space remains available in the pre-allocated client cache older cached data may be removed and newer data may be retained in anticipation of the receipt of new image data from server 160.

In some embodiments, the cache agent 140 running on client system 170 is configured to periodically receive new image data, such as at a certain time each day. In some embodiments, the cache agent 140 is configured to receive new image data as soon as it becomes available on server 160 (i.e. as soon as newly scanned images and/or patient cases are received by the server and prepared for transmittal). With reference to FIG. 6, requests may be received from a remote server 160 (step 620), and the remote server 160 may check to see if the cache agent 140 is installed and/or running on the client system 170. In some embodiments, an authentication is performed (step 630) (see also FIG. 4B). Following the establishment of an authenticated session between the cache agent 140 and the client system 170, stored image data may be received by the cache agent 140 for storage in the pre-allocated client cache (step 640).

Figure 7:
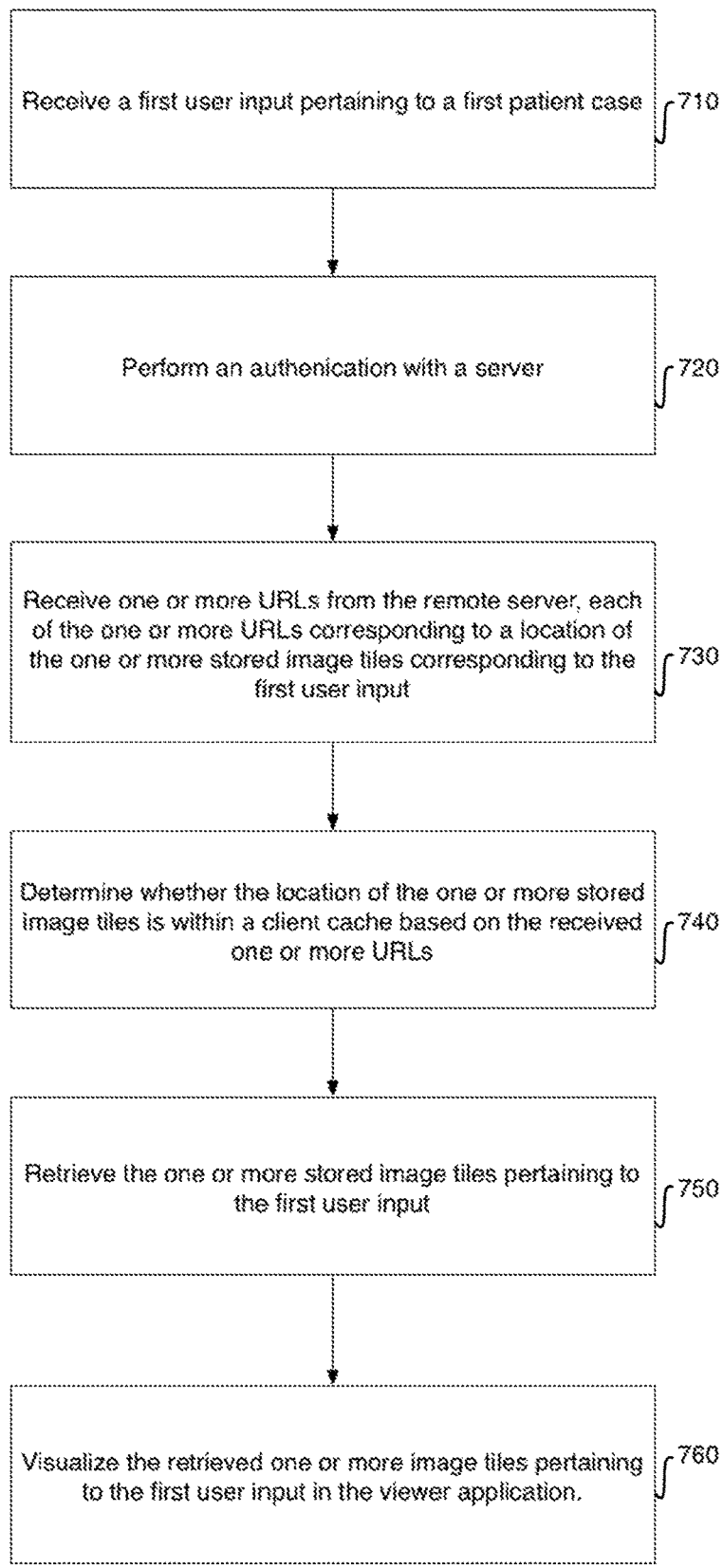
FIG. 7 sets forth a flowchart providing the steps of visualizing image data corresponding to received user inputs, such as input received by a user interacting with a viewer application directly or indirectly through a browser in accordance with some embodiments.
Figure 8:
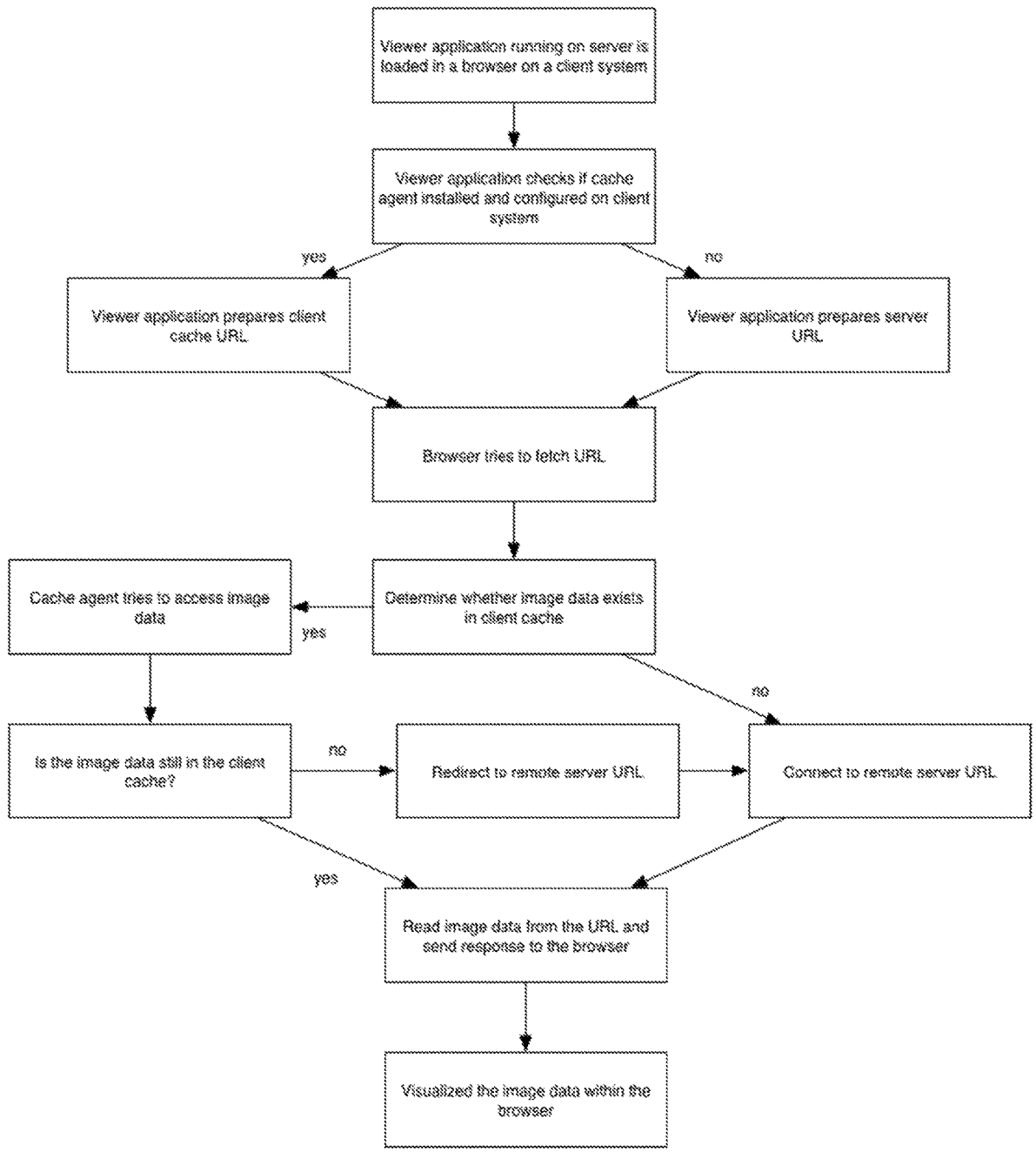
FIG. 8 sets forth a flowchart providing the steps of visualizing image data corresponding to received user inputs, such as input received by a user interacting with a browser in accordance with some embodiments.

The image data within the client cache may then be accessed by the client system 170 for visualization after a request for image data has been received from a user (see FIGS. 7 and 8). With reference to FIG. 7, in a first step, the viewer application 120 receives a first user input pertaining to the selection of image data, e.g. a user input where additional tiles are needed to complete a panning operation (step 710). In some embodiments, the viewer application 120 is run on the client system 170. In some embodiments, the viewer application 120 is run on the remote sever 160 but an instance of the viewer application accessed via a browser 195 on client system 170. If the viewer application is accessed through a browser, then the browser may receive user inputs and those user inputs may be transmitted remotely.

Subsequently, a request for image data is transmitted from the viewer application 120 to a remote server 160. In some embodiments, an authentication is performed between the client system 170 and the remote server 160 (step 720) and the client system 170 may transmit signals to the remote server 160 that a cache agent 140 is running on the client system 170. In some embodiments, the remote server 160 then sends one or more URLs to the viewer application 120, where each of the one or more URLs provide location information as to where the request image data is stored (step 730). In some embodiments, a determination is made by the viewer application 120 as to whether the requested image data is present in the client cache (step 740). In some embodiments, the viewer application 120, based on the URLs provided and assuming that the image data is stored in the client cache, may retrieve that image data directly from the client cache (step 750). In some embodiments, the cache agent 140 retrieves the image data from the client cache based on instructions received from the viewer application 120. In some embodiments, the viewer application 120, based on the URLs provided, is redirected to a remote server (or a reverse proxy running on the remote server) for the requested image data (step 750) (in this instance, the image data is not found in cache, if it was removed by the cache agent 140 during client cache maintenance). Once the image data is received by the viewer application 120, it is visualized (step 760). The processes is repeated as new user inputs are received, such as second, third, and fourth user inputs. The process is also repeated for each patient case viewed by the user.

With reference to FIG. 8, in some embodiments, a viewer application is run remotely on server 160 and an instance of the viewer application is loaded into a browser running locally on client system 170. In this way, a user will use the viewer application in the same manner as if it were running locally on client system 170. In this regard, user inputs made within the viewer loaded into the browser will cause the viewer application to retrieve requested image data, after performing an authentication and a check to see if the cache agent 140 is running on client system 170. The remotely run viewer application will then send one or more URLs to the browser, and the browser will attempt to fetch those URLs, such as from within a client cache on the client system (and through the cache agent 140 running on client system 170). If the image data exists in a local client cache, the browser will retrieve the image from that cache. If not, the browser will be redirected to a remote sever (e.g. a reverse proxy) where the image data will be retrieved. In either case, the retrieved image data will be loaded and visualized.

In some embodiments, an authentication is performed between the client system and the remote server and the client system may transmit signals to the remote server that a cache agent is running on the client system. In some embodiments, the remote server may then send one or more URLs to the browser running on the client system, where each of the one or more URLs provide location information as to where the request image data is stored. In some embodiments, a determination is made by the browser as to whether the requested image data is present in the client cache. In some embodiments, the browser, based on the URLs provided and assuming that the image data is stored in the client cache, may retrieve that image data directly from the client cache (such as through the cache agent running on the client system). In some embodiments, the browser, based on the URLs provided, is redirected to a remote server (or a reverse proxy running on the remote server) for the requested image data (in this instance, the image data is not found in cache, if it was removed by the cache agent during client cache maintenance). Once the image data is received by the browser, it is visualized. The processes is repeated as new user inputs are received, such as second, third, and fourth user inputs. The process is also repeated for each patient case viewed by the user.

Additional Embodiments

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor(s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method of pre-processing biological image data on a server to facilitate transmission of the biological image data to a digital pathology analysis system, the method comprising:
receiving the biological image data having a first image file format, the biological image data derived from scans of microscope slides having one or more biological samples disposed thereon, the biological samples stained with hematoxylin and eosin or stained to identify presence of one or more biomarkers;
pre-processing the received biological image data to generate one or more pre-processed image files, wherein each of the generated one or more pre-processed image files is derived from the received biological image data in the first image file format, and wherein each of the generated one or more pre-processed image files are provided in a second file format;
storing the generated one or more pre-processed image files provided in the second file format in one or more memories communicatively coupled to the server; and
transmitting, prior to a user request, at least one pre-processed image file of the generated one or more pre-processed image files to a cache agent running on a client system, wherein the cache agent is an application configured to manage preprocessed files on the client system, such that the at least one pre-processed image file is retrievable locally from a storage subsystem of the client system upon receiving a user input requiring the at least one pre-processed image file.

2. The method of claim 1, wherein the first image file format and the second image file format are the same.

3. The method of claim 2, wherein the pre-processing step generates a plurality of pre-processed image files.

4. The method of claim 3, wherein the plurality of pre-processed image files are a plurality of image tile files, and wherein the plurality of image tile files each comprise a file name comprising coordinates corresponding to a position of an individual tile file within the received biological image data having the first image file format.

5. The method of claim 2, wherein the pre-processing step generates multiple sets of pre-processed image files, wherein each set of pre-processed image files of the multiple sets of pre-processed image files comprises a plurality of image tile files corresponding to a single magnification level.

6. The method of claim 2, wherein the first image file format and the second image file format are compressed image file formats.

7. The method of claim 6, wherein the compressed image file formats are selected from the group consisting of JPEG File Interchange Format, portable network graphics file format, and derivates thereof.

8. The method of claim 1, wherein the first image file format and the second image file format are different.

9. The method of claim 8, wherein the first image file format is one of a RAW image file format or an uncompressed image file format; and wherein the second image file format is a compressed image file format.

10. The method of claim 9, wherein the pre-processing step comprises converting the received biological image data in the RAW or uncompressed image file format and generating the one or more pre-processed image files in the compressed image file format.

11. The method of claim 10, wherein the pre-processing step generates a single pre-processed image file in the compressed image file format.

12. The method of claim 10, wherein the pre-processing step generates a plurality of pre-processed image files in the compressed image file format.

13. The method of claim 12, wherein the pre-processing step generates multiple sets of pre-processed image files, wherein each set of pre-processed image files of the multiple sets of pre-processed image files comprises a plurality of image tile files in the compressed image file format corresponding to a single magnification level.

14. The method of claim 12, wherein the plurality of pre-processed image files are a plurality of image tile files, and wherein the plurality of image tile files each comprise a file name comprising coordinates corresponding to a position of an individual tile file within the received biological image data having the first image file format.

15. The method of 12, wherein a file size of received biological image data having the first image file format is greater than an aggregate file size of all of the generated plurality of the pre-processed image files in the compressed image file format.

16. The method of claim 9, wherein the compressed image file format is a destination file format.

17. The method of claim 16, wherein the destination file format is a browser compatible file format.

18. A system comprising:
one or more processors;
a memory coupled to the one or more processors, the memory storing a plurality of instructions executable by the one or more processors, the plurality of instructions comprising instructions that when executed by the one or more processors cause the one or more processors to perform operations comprising:
receiving biological image data having a first image file format, the biological image data derived from scans of microscope slides having one or more biological samples disposed thereon, the biological samples stained with hematoxylin and eosin or stained to identify presence of one or more biomarkers;
pre-processing the received biological image data to generate one or more pre-processed image files, wherein each of the generated one or more pre-processed image files is derived from the received biological image data in the first image file format, and wherein each of the generated one or more pre-processed image files are provided in a second file format;
storing the generated one or more pre-processed image files provided in the second file format in one or more memories communicatively coupled to a server; and
transmitting, prior to a user request, at least one pre-processed image file of the generated one or more pre-processed image files to a cache agent running on a client system wherein the cache agent is an application configured to manage preprocessed files on the client system, such that the at least one pre-processed image file is retrievable locally from a storage subsystem of the client system upon receiving a user input requiring the at least one pre-processed image file.

19. The system of claim 18, wherein the first image file format and the second image file format are different.

20. The system of claim 19, wherein the first image file format is one of a RAW image file format or an uncompressed image file format; and wherein the second image file format is a compressed image file format.

21. The system of claim 20, wherein the transmitting of the at least one pre-processed image file is performed in response to completing the pre-processing of the received biological image data.

22. A non-transitory computer-readable memory storing a plurality of instructions executable by one or more processors, the plurality of instructions comprising instructions that when executed by the one or more processors cause the one or more processors to perform operations comprising:
   receiving the biological image data having a first image file format, the biological image data derived from scans of microscope slides having one or more biological samples disposed thereon, the biological samples stained with hematoxylin and eosin or stained to identify presence of one or more biomarkers;
   pre-processing the received biological image data to generate one or more pre-processed image files, wherein each of the generated one or more pre-processed image files is derived from the received biological image data in the first image file format, and wherein each of the generated one or more pre-processed image files are provided in a second file format;
   storing the generated one or more pre-processed image files provided in the second file format in one or more memories communicatively coupled to the server; and
   transmitting, prior to a user request, at least one pre-processed image file of the generated one or more pre-processed image files to a cache agent running on a client system, wherein the cache agent is an application configured to manage preprocessed files on the client system, such that the at least one pre-processed image file is retrievable locally from a storage subsystem of the client system upon receiving a user input requiring the at least one pre-processed image file.

23. The non-transitory computer-readable memory of claim 22, wherein the first image file format and the second image file format are different.

24. The non-transitory computer-readable memory of claim 23, wherein the first image file format is one of a RAW image file format or an uncompressed image file format; and wherein the second image file format is a compressed image file format.

25. The non-transitory computer-readable memory of claim 24, wherein the transmitting of the at least one pre-processed image file is performed in response to completing the pre-processing of the received biological image data.

* * * * *